US008267969B2

(12) United States Patent
Altarac et al.

(10) Patent No.: US 8,267,969 B2
(45) Date of Patent: Sep. 18, 2012

(54) SCREW SYSTEMS AND METHODS FOR USE IN STABILIZATION OF BONE STRUCTURES

(75) Inventors: Moti Altarac, Irvine, CA (US); Stanley Kyle Hayes, Mission Viejo, CA (US); Joey Camia Reglos, Lake Forest, CA (US); Daniel H. Kim, Los Altos, CA (US); J. Christopher Flaherty, Topsfiled, MA (US)

(73) Assignee: Exactech, Inc., Gainesville, FL (US)

( * ) Notice: Subject to any disclaimer, the term of this patent is extended or adjusted under 35 U.S.C. 154(b) by 1085 days.

(21) Appl. No.: 11/726,093

(22) Filed: Mar. 20, 2007

(65) Prior Publication Data
US 2007/0167949 A1    Jul. 19, 2007

Related U.S. Application Data

(63) Continuation-in-part of application No. 11/427,738, filed on Jun. 29, 2006, now Pat. No. 7,935,134, which is a continuation-in-part of application No. 11/436,407, filed on May 17, 2006, now Pat. No. 8,025,680, which is a continuation-in-part of application No. 11/033,452, filed on Jan. 10, 2005, now Pat. No. 7,998,175, which is a continuation-in-part of application No. 11/006,495, filed on Dec. 6, 2004, now Pat. No. 8,075,595, which is a continuation-in-part of application No. 10/970,366, filed on Oct. 20, 2004, now Pat. No. 8,162,985, said application No. 11/427,738 is a continuation-in-part of application No. 11/362,366, filed on Feb. 23, 2006, application No. 11/726,093, which is a continuation-in-part of application No. 11/586,849, filed on Oct. 25, 2006, which is a continuation-in-part of application No. 11/362,366, filed on Feb. 23, 2006.

(60) Provisional application No. 60/701,660, filed on Jul. 22, 2005.

(51) Int. Cl.
*A61B 17/70* (2006.01)
(52) U.S. Cl. ........................................ 606/269; 606/270
(58) Field of Classification Search .......... 606/264–275, 606/301–320
See application file for complete search history.

(56) References Cited

U.S. PATENT DOCUMENTS
602,580 A    4/1898    Haskins et al.
(Continued)

FOREIGN PATENT DOCUMENTS
EP    767636    1/1999
(Continued)

OTHER PUBLICATIONS
Co-pending U.S. Appl. No. 11/436,407.
(Continued)

*Primary Examiner* — Eduardo C Robert
*Assistant Examiner* — Jerry Cumberledge
(74) *Attorney, Agent, or Firm* — Meyertons, Hood, Kivlin, Kowert & Goetzel, P.C.; Eric B. Meyertons

(57) ABSTRACT

Methods, systems, devices and tools for placing bone stabilization components in a patient are provided. The systems and devices have a reduced number of discrete components that allow placement through small incisions and tubes. More particularly, the present invention is directed to screws for use in systems and methods of treating the spine, which eliminate pain and enable spinal motion, which effectively mimics that of a normally functioning spine. Methods are also provided for installation of the screw and other subject systems.

68 Claims, 15 Drawing Sheets

U.S. PATENT DOCUMENTS

| | | |
|---|---|---|
| 802,844 A | 10/1905 | Covell et al. |
| 2,790,437 A | 4/1957 | Moore |
| 4,545,374 A | 10/1985 | Jacobson |
| 4,611,582 A | 9/1986 | Duff |
| 4,743,260 A | 5/1988 | Burton |
| 4,858,601 A | 8/1989 | Glisson |
| 4,959,064 A | 9/1990 | Engelhardt |
| 5,015,247 A | 5/1991 | Michelson |
| 5,062,845 A | 11/1991 | Kuslich et al. |
| 5,092,866 A | 3/1992 | Breard et al. |
| 5,129,388 A | 7/1992 | Vianaud et al. |
| 5,171,279 A | 12/1992 | Mathews |
| 5,180,393 A | 1/1993 | Commarmond |
| 5,207,678 A | 5/1993 | Harms et al. |
| 5,282,863 A | 2/1994 | Burton |
| 5,368,594 A | 11/1994 | Martin et al. |
| 5,370,646 A | 12/1994 | Reese et al. |
| 5,375,823 A | 12/1994 | Navas |
| 5,387,212 A | 2/1995 | Yuan et al. |
| 5,415,661 A | 5/1995 | Holmes |
| 5,437,669 A | 8/1995 | Yuan et al. |
| 5,437,672 A | 8/1995 | Alleyne |
| 5,443,467 A | 8/1995 | Biedermann |
| 5,449,355 A | 9/1995 | Rhum et al. |
| 5,474,555 A | 12/1995 | Puno et al. |
| 5,480,401 A | 1/1996 | Navas |
| 5,484,437 A | 1/1996 | Michelson |
| 5,489,308 A | 2/1996 | Kuslich et al. |
| 5,522,843 A | 6/1996 | Zang |
| 5,527,312 A | 6/1996 | Ray |
| 5,540,688 A | 7/1996 | Navas |
| 5,571,191 A | 11/1996 | Fitz |
| 5,609,636 A | 3/1997 | Kohrs et al. |
| 5,616,142 A | 4/1997 | Yuan et al. |
| 5,645,599 A | 7/1997 | Samani et al. |
| 5,658,337 A | 8/1997 | Kohrs et al. |
| 5,672,175 A | 9/1997 | Martin |
| 5,720,751 A | 2/1998 | Jackson |
| 5,741,253 A | 4/1998 | Michelson |
| 5,776,135 A | 7/1998 | Errico et al. |
| 5,885,286 A | 3/1999 | Sherman et al. |
| 5,891,145 A * | 4/1999 | Morrison et al. ............ 606/266 |
| RE36,211 E | 5/1999 | Nonomura |
| 5,964,761 A | 10/1999 | Kambin |
| 6,004,327 A | 12/1999 | Asnis et al. |
| 6,014,588 A | 1/2000 | Fitz |
| 6,033,406 A | 3/2000 | Mathews |
| 6,063,088 A | 5/2000 | Winslow |
| RE36,758 E | 6/2000 | Fitz |
| 6,080,155 A | 6/2000 | Michelson |
| 6,080,157 A | 6/2000 | Cathro et al. |
| 6,096,038 A | 8/2000 | Michelson |
| 6,132,464 A | 10/2000 | Martin |
| 6,200,322 B1 | 3/2001 | Branch et al. |
| 6,241,730 B1 | 6/2001 | Alby |
| 6,248,105 B1 * | 6/2001 | Schlapfer et al. ............ 606/266 |
| 6,261,293 B1 | 7/2001 | Nicholson et al. |
| 6,264,656 B1 | 7/2001 | Michelson |
| 6,267,764 B1 | 7/2001 | Elberg |
| 6,267,765 B1 | 7/2001 | Taylor et al. |
| 6,270,498 B1 | 8/2001 | Michelson |
| 6,287,764 B1 | 9/2001 | Hildebrand et al. |
| 6,290,724 B1 | 9/2001 | Marino |
| 6,304,140 B1 | 10/2001 | Thron et al. |
| 6,306,140 B1 | 10/2001 | Siddiqui |
| 6,348,053 B1 | 2/2002 | Cachia |
| 6,375,657 B1 | 4/2002 | Doubler et al. |
| 6,379,354 B1 | 4/2002 | Rogozinski et al. |
| 6,419,703 B1 | 7/2002 | Fallin et al. |
| 6,440,133 B1 | 8/2002 | Beale et al. |
| 6,478,798 B1 | 11/2002 | Howland |
| 6,485,491 B1 | 11/2002 | Farris et al. |
| 6,485,518 B1 | 11/2002 | Cornwall et al. |
| 6,530,929 B1 | 3/2003 | Justis et al. |
| 6,533,790 B1 | 3/2003 | Liu |
| 6,540,747 B1 | 4/2003 | Marino |
| 6,547,795 B2 | 4/2003 | Schneiderman |
| 6,554,830 B1 | 4/2003 | Chappius |
| 6,558,390 B2 | 5/2003 | Cragg |
| 6,562,046 B2 | 5/2003 | Sasso |
| 6,565,565 B1 * | 5/2003 | Yuan et al. ............ 606/272 |
| 6,565,573 B1 | 5/2003 | Ferrante et al. |
| 6,565,605 B2 | 5/2003 | Goble et al. |
| 6,579,319 B2 | 6/2003 | Goble et al. |
| 6,610,091 B1 | 8/2003 | Reiley |
| 6,626,904 B1 | 9/2003 | Jammet et al. |
| 6,626,905 B1 | 9/2003 | Schmiel et al. |
| 6,626,944 B1 | 9/2003 | Taylor et al. |
| 6,645,207 B2 | 11/2003 | Dixon et al. |
| 6,645,248 B2 | 11/2003 | Casutt |
| 6,648,888 B1 | 11/2003 | Shluzas |
| 6,660,006 B2 | 12/2003 | Markworth et al. |
| 6,669,697 B1 | 12/2003 | Pisharodi |
| 6,669,729 B2 | 12/2003 | Chin |
| 6,676,661 B1 | 1/2004 | Martin Benlloch et al. |
| 6,695,842 B2 | 2/2004 | Zucherman et al. |
| 6,699,247 B2 | 3/2004 | Zucherman et al. |
| 6,702,817 B2 | 3/2004 | Beger et al. |
| 6,709,434 B1 | 3/2004 | Gournay et al. |
| 6,716,214 B1 | 4/2004 | Jackson |
| 6,716,245 B2 | 4/2004 | Pasquet et al. |
| 6,726,687 B2 | 4/2004 | Jackson |
| 6,726,689 B2 | 4/2004 | Jackson |
| 6,730,089 B2 | 5/2004 | Jackson |
| 6,740,086 B2 | 5/2004 | Richelsoph |
| 6,740,090 B1 | 5/2004 | Cragg et al. |
| 6,749,613 B1 | 6/2004 | Conchy et al. |
| 6,749,614 B2 | 6/2004 | Teitelbaum et al. |
| 6,761,720 B1 | 7/2004 | Seneqas et al. |
| 6,770,075 B2 | 8/2004 | Howland |
| 6,783,527 B2 | 8/2004 | Drewry et al. |
| 6,786,903 B2 * | 9/2004 | Lin ........................ 606/23 |
| 6,790,209 B2 | 9/2004 | Beale et al. |
| 6,793,656 B1 | 9/2004 | Mathews |
| 6,802,844 B2 | 10/2004 | Ferree |
| 6,802,845 B2 | 10/2004 | Shirado et al. |
| 6,805,697 B1 | 10/2004 | Helm et al. |
| 6,811,567 B2 | 11/2004 | Reiley |
| 6,821,277 B2 | 11/2004 | Teitelbaum |
| 6,835,205 B2 | 12/2004 | Atkinson et al. |
| 6,835,207 B2 | 12/2004 | Zacouto et al. |
| 6,869,433 B2 | 3/2005 | Glascott |
| 6,875,212 B2 | 4/2005 | Shaolian et al. |
| 6,875,222 B2 | 4/2005 | Long et al. |
| 6,884,244 B1 | 4/2005 | Jackson |
| 6,896,677 B1 * | 5/2005 | Lin ........................ 606/266 |
| 6,899,716 B2 | 5/2005 | Cragg |
| 6,902,580 B2 | 6/2005 | Fallin et al. |
| 6,949,123 B2 | 9/2005 | Reiley |
| 6,966,910 B2 | 11/2005 | Ritland |
| 6,966,930 B2 | 11/2005 | Arnin et al. |
| 6,974,478 B2 | 12/2005 | Reiley et al. |
| 6,989,011 B2 | 1/2006 | Paul et al. |
| 6,997,927 B2 | 2/2006 | Jackson |
| 7,008,422 B2 | 3/2006 | Foley et al. |
| 7,011,660 B2 | 3/2006 | Sherman et al. |
| 7,011,685 B2 | 3/2006 | Arnin et al. |
| 7,029,475 B2 | 4/2006 | Panjabi |
| 7,033,358 B2 | 4/2006 | Taylor et al. |
| 7,041,136 B2 | 5/2006 | Goble et al. |
| 7,051,451 B2 | 5/2006 | Augostino et al. |
| 7,052,497 B2 | 5/2006 | Sherman et al. |
| 7,060,068 B2 | 6/2006 | Tromanhauser et al. |
| 7,066,939 B2 | 6/2006 | Taylor |
| 7,066,957 B2 | 6/2006 | Graf et al. |
| 7,070,598 B2 | 7/2006 | Lim et al. |
| 7,074,237 B2 | 7/2006 | Goble et al. |
| 7,074,238 B2 | 7/2006 | Stinson et al. |
| 7,079,883 B2 | 7/2006 | Marino et al. |
| 7,081,117 B2 | 7/2006 | Bono et al. |
| 7,083,621 B2 | 8/2006 | Shaolian et al. |
| 7,083,622 B2 | 8/2006 | Simonson |
| 7,083,649 B2 | 8/2006 | Zucherman et al. |
| 7,087,055 B2 | 8/2006 | Lim et al. |
| 7,087,057 B2 | 8/2006 | Konieczynski et al. |
| 7,087,084 B2 | 8/2006 | Reiley |
| 7,090,698 B2 | 8/2006 | Goble et al. |

| Patent/Publication | Date | Name |
|---|---|---|
| 7,101,398 B2 | 9/2006 | Dooris et al. |
| 7,108,705 B2 | 9/2006 | Davison et al. |
| 7,125,410 B2 | 10/2006 | Freudiger et al. |
| 7,125,426 B2 | 10/2006 | Moumene et al. |
| 7,128,743 B2 | 10/2006 | Metz-Stavenhagen |
| 7,137,985 B2 | 11/2006 | Jahng |
| 7,141,051 B2 * | 11/2006 | Janowski et al. ............ 606/272 |
| 7,156,849 B2 | 1/2007 | Dunbar et al. |
| 7,160,300 B2 | 1/2007 | Jackson |
| 7,182,783 B2 | 2/2007 | Trieu |
| 7,188,626 B2 | 3/2007 | Foley et al. |
| 7,204,853 B2 | 4/2007 | Gordon et al. |
| 7,207,992 B2 | 4/2007 | Ritland |
| 7,214,227 B2 | 5/2007 | Colleran et al. |
| 7,220,262 B1 | 5/2007 | Hynes |
| 7,229,441 B2 | 6/2007 | Trieu et al. |
| 7,250,052 B2 | 7/2007 | Landry et al. |
| 7,261,688 B2 | 8/2007 | Smith et al. |
| 7,278,995 B2 | 10/2007 | Nichols et al. |
| 7,282,065 B2 | 10/2007 | Kirschman |
| 7,291,150 B2 | 11/2007 | Graf et al. |
| 7,291,153 B2 | 11/2007 | Glascott |
| 7,294,129 B2 | 11/2007 | Hawkins et al. |
| 7,306,603 B2 | 12/2007 | Boehm, Jr. et al. |
| 7,329,258 B2 | 2/2008 | Studer et al. |
| 7,335,200 B2 | 2/2008 | Carli et al. |
| 7,354,453 B2 | 4/2008 | McAfee |
| 7,361,196 B2 | 4/2008 | Fallin et al. |
| 7,371,238 B2 | 5/2008 | Soboleski et al. |
| 7,377,921 B2 | 5/2008 | Studer et al. |
| 7,377,942 B2 | 5/2008 | Berry |
| 7,406,775 B2 | 8/2008 | Funk et al. |
| 7,445,635 B2 | 11/2008 | Fallin et al. |
| 7,465,306 B2 | 12/2008 | Pond, Jr. et al. |
| 7,470,279 B2 | 12/2008 | Jackson |
| 7,476,238 B2 | 1/2009 | Panjabi |
| 7,491,218 B2 | 2/2009 | Landry et al. |
| 7,493,019 B2 | 2/2009 | Moon et al. |
| 7,503,918 B2 | 3/2009 | Baccelli et al. |
| 7,527,638 B2 | 5/2009 | Anderson et al. |
| 7,547,318 B2 | 6/2009 | Birkmeyer et al. |
| 7,563,264 B2 | 7/2009 | Landry et al. |
| 7,588,575 B2 | 9/2009 | Colleran et al. |
| 7,588,588 B2 | 9/2009 | Spitler et al. |
| 7,591,839 B2 * | 9/2009 | Biedermann et al. ......... 606/266 |
| 7,615,068 B2 | 11/2009 | Timm et al. |
| 7,618,442 B2 * | 11/2009 | Spitler et al. ................... 606/266 |
| 7,635,379 B2 | 12/2009 | Callahan et al. |
| 7,662,172 B2 | 2/2010 | Warnick |
| 7,678,137 B2 | 3/2010 | Butler et al. |
| 7,699,875 B2 | 4/2010 | Timm |
| 7,713,287 B2 | 5/2010 | Timm et al. |
| 7,713,288 B2 | 5/2010 | Timm et al. |
| 7,935,134 B2 | 5/2011 | Reqlos et al. |
| 8,025,680 B2 | 9/2011 | Hayes et al. |
| 8,096,996 B2 | 1/2012 | Gutierrez et al. |
| 8,226,690 B2 | 7/2012 | Altarac et al. |
| 2001/0037111 A1 | 11/2001 | Dixon et al. |
| 2002/0026193 A1 | 2/2002 | Barker et al. |
| 2002/0032443 A1 | 3/2002 | Sherman et al. |
| 2002/0065557 A1 | 5/2002 | Goble et al. |
| 2002/0068975 A1 | 6/2002 | Teitelbaum et al. |
| 2002/0072800 A1 | 6/2002 | Goble et al. |
| 2002/0082599 A1 | 6/2002 | Crandall et al. |
| 2002/0082600 A1 | 6/2002 | Shaolian et al. |
| 2002/0091390 A1 | 7/2002 | Michelson |
| 2002/0095154 A1 | 7/2002 | Atkinson |
| 2002/0123806 A1 | 9/2002 | Reiley |
| 2002/0133154 A1 | 9/2002 | Saint Martin |
| 2002/0133155 A1 | 9/2002 | Ferree |
| 2002/0151895 A1 | 10/2002 | Soboleski et al. |
| 2002/0161368 A1 | 10/2002 | Foley et al. |
| 2002/0161370 A1 | 10/2002 | Frigg et al. |
| 2002/0173971 A1 | 11/2002 | Stirpe et al. |
| 2002/0183748 A1 | 12/2002 | Martin et al. |
| 2002/0198526 A1 | 12/2002 | Shaolian et al. |
| 2003/0004511 A1 | 1/2003 | Ferree |
| 2003/0004512 A1 | 1/2003 | Farris et al. |
| 2003/0004572 A1 | 1/2003 | Goble et al. |
| 2003/0018350 A1 | 1/2003 | Zucherman et al. |
| 2003/0023240 A1 | 1/2003 | Amrein et al. |
| 2003/0028250 A1 | 2/2003 | Reiley et al. |
| 2003/0032957 A1 | 2/2003 | McKinley |
| 2003/0032965 A1 | 2/2003 | Schneiderman |
| 2003/0040797 A1 | 2/2003 | Fallin et al. |
| 2003/0045878 A1 | 3/2003 | Petit et al. |
| 2003/0055426 A1 | 3/2003 | Carbone et al. |
| 2003/0055427 A1 | 3/2003 | Graf |
| 2003/0073996 A1 | 4/2003 | Doubler et al. |
| 2003/0073997 A1 | 4/2003 | Doubler et al. |
| 2003/0073998 A1 | 4/2003 | Pagliuca et al. |
| 2003/0125741 A1 | 7/2003 | Biedermann et al. |
| 2003/0149431 A1 | 8/2003 | Varieur |
| 2003/0153912 A1 | 8/2003 | Graf |
| 2003/0163133 A1 | 8/2003 | Altarac et al. |
| 2003/0171749 A1 | 9/2003 | Le Couedic et al. |
| 2003/0171750 A1 | 9/2003 | Chin |
| 2003/0199872 A1 | 10/2003 | Markworth et al. |
| 2003/0208202 A1 | 11/2003 | Falahee |
| 2003/0208203 A1 | 11/2003 | Lim et al. |
| 2003/0216735 A1 | 11/2003 | Altarac et al. |
| 2003/0220643 A1 | 11/2003 | Ferree |
| 2003/0229347 A1 | 12/2003 | Sherman et al. |
| 2004/0002708 A1 | 1/2004 | Ritland |
| 2004/0006341 A1 | 1/2004 | Shaolian et al. |
| 2004/0006344 A1 | 1/2004 | Nguyen et al. |
| 2004/0006391 A1 | 1/2004 | Reiley |
| 2004/0039384 A1 | 2/2004 | Boehm |
| 2004/0049189 A1 | 3/2004 | Le Couedic et al. |
| 2004/0049281 A1 | 3/2004 | Reiley |
| 2004/0064140 A1 | 4/2004 | Taylor et al. |
| 2004/0080418 A1 | 4/2004 | Dahlborn et al. |
| 2004/0082954 A1 | 4/2004 | Teitelbaum et al. |
| 2004/0087947 A1 | 5/2004 | Lim et al. |
| 2004/0092931 A1 | 5/2004 | Taylor et al. |
| 2004/0097933 A1 * | 5/2004 | Lourdel et al. .................. 606/61 |
| 2004/0116927 A1 | 6/2004 | Graf |
| 2004/0127989 A1 | 7/2004 | Dooris et al. |
| 2004/0133208 A1 | 7/2004 | Weikel et al. |
| 2004/0138662 A1 | 7/2004 | Landry et al. |
| 2004/0143265 A1 | 7/2004 | Landry et al. |
| 2004/0143270 A1 | 7/2004 | Zucherman et al. |
| 2004/0147928 A1 | 7/2004 | Landry et al. |
| 2004/0147936 A1 | 7/2004 | Rosenberg et al. |
| 2004/0147937 A1 | 7/2004 | Dunbar et al. |
| 2004/0215190 A1 | 10/2004 | Nguyen et al. |
| 2004/0225289 A1 | 11/2004 | Biedermann et al. |
| 2004/0230201 A1 | 11/2004 | Yuan et al. |
| 2004/0230304 A1 | 11/2004 | Yuan et al. |
| 2004/0236328 A1 | 11/2004 | Paul et al. |
| 2004/0236329 A1 | 11/2004 | Panjabi |
| 2004/0243126 A1 | 12/2004 | Carbone et al. |
| 2004/0249378 A1 | 12/2004 | Saint Martin et al. |
| 2004/0249380 A1 | 12/2004 | Glascott |
| 2004/0267260 A1 | 12/2004 | Mack et al. |
| 2005/0010217 A1 | 1/2005 | Dalton |
| 2005/0010953 A1 | 1/2005 | Carney et al. |
| 2005/0010954 A1 | 1/2005 | Binder |
| 2005/0010956 A1 | 1/2005 | Moon et al. |
| 2005/0021031 A1 | 1/2005 | Foley et al. |
| 2005/0027361 A1 | 2/2005 | Reiley |
| 2005/0033295 A1 | 2/2005 | Wisnewski |
| 2005/0033434 A1 | 2/2005 | Berry |
| 2005/0033436 A1 | 2/2005 | Schlapfer et al. |
| 2005/0033439 A1 | 2/2005 | Gordon et al. |
| 2005/0038429 A1 | 2/2005 | Elsebaie |
| 2005/0038430 A1 | 2/2005 | McKinley |
| 2005/0038432 A1 | 2/2005 | Shaolian et al. |
| 2005/0038440 A1 | 2/2005 | Larson et al. |
| 2005/0043742 A1 | 2/2005 | Bruneau et al. |
| 2005/0043797 A1 | 2/2005 | Lee |
| 2005/0043799 A1 | 2/2005 | Reiley |
| 2005/0049588 A1 | 3/2005 | Jackson |
| 2005/0049589 A1 | 3/2005 | Jackson |
| 2005/0049705 A1 | 3/2005 | Hale et al. |
| 2005/0049708 A1 | 3/2005 | Atkinson et al. |
| 2005/0055031 A1 | 3/2005 | Lim |
| 2005/0055096 A1 | 3/2005 | Serhan et al. |

| | | |
|---|---|---|
| 2005/0065515 A1 | 3/2005 | Jahng |
| 2005/0065516 A1 | 3/2005 | Jahng |
| 2005/0065517 A1 | 3/2005 | Chin |
| 2005/0070917 A1 | 3/2005 | Justis |
| 2005/0080418 A1 | 4/2005 | Simonson et al. |
| 2005/0080486 A1 | 4/2005 | Fallin et al. |
| 2005/0085813 A1 | 4/2005 | Spitler et al. |
| 2005/0085815 A1 | 4/2005 | Harms et al. |
| 2005/0101953 A1 | 5/2005 | Simonson |
| 2005/0101954 A1 | 5/2005 | Simonson |
| 2005/0101956 A1 | 5/2005 | Simonson |
| 2005/0113832 A1 | 5/2005 | Molz, IV et al. |
| 2005/0113927 A1 | 5/2005 | Malek |
| 2005/0119748 A1 | 6/2005 | Reiley et al. |
| 2005/0124991 A1 | 6/2005 | Jahng |
| 2005/0125066 A1 | 6/2005 | McAfee |
| 2005/0131405 A1 | 6/2005 | Molz et al. |
| 2005/0131406 A1 | 6/2005 | Reiley et al. |
| 2005/0131407 A1 | 6/2005 | Sicvol et al. |
| 2005/0131408 A1 | 6/2005 | Sicvol et al. |
| 2005/0131409 A1 | 6/2005 | Chervitz et al. |
| 2005/0131422 A1 | 6/2005 | Anderson et al. |
| 2005/0131537 A1 | 6/2005 | Hoy et al. |
| 2005/0131538 A1 | 6/2005 | Chervitz et al. |
| 2005/0131545 A1 | 6/2005 | Chervitz et al. |
| 2005/0137602 A1 | 6/2005 | Assell et al. |
| 2005/0143737 A1 | 6/2005 | Pafford et al. |
| 2005/0143823 A1 | 6/2005 | Boyd et al. |
| 2005/0149020 A1 | 7/2005 | Jahng |
| 2005/0149036 A1 | 7/2005 | Varieur et al. |
| 2005/0149053 A1 | 7/2005 | Varieur et al. |
| 2005/0154389 A1 | 7/2005 | Selover et al. |
| 2005/0154390 A1 | 7/2005 | Biedermann et al. |
| 2005/0154461 A1 | 7/2005 | Humphreys et al. |
| 2005/0154464 A1 | 7/2005 | Humphreys et al. |
| 2005/0154465 A1 | 7/2005 | Hodges et al. |
| 2005/0154466 A1 | 7/2005 | Humphreys et al. |
| 2005/0154467 A1 | 7/2005 | Peterman et al. |
| 2005/0165396 A1 | 7/2005 | Fortin et al. |
| 2005/0171543 A1 | 8/2005 | Timm et al. |
| 2005/0171608 A1 | 8/2005 | Peterman et al. |
| 2005/0171609 A1 | 8/2005 | Humphreys et al. |
| 2005/0171610 A1 | 8/2005 | Humphreys et al. |
| 2005/0177156 A1 | 8/2005 | Timm et al. |
| 2005/0177157 A1 | 8/2005 | Jahng |
| 2005/0177164 A1 | 8/2005 | Walters et al. |
| 2005/0177166 A1 | 8/2005 | Timm et al. |
| 2005/0177240 A1 | 8/2005 | Blain |
| 2005/0182400 A1 | 8/2005 | White |
| 2005/0182401 A1 | 8/2005 | Timm et al. |
| 2005/0182409 A1 | 8/2005 | Callahan et al. |
| 2005/0187548 A1 | 8/2005 | Butler |
| 2005/0192570 A1 | 9/2005 | Jackson |
| 2005/0192574 A1 | 9/2005 | Blain |
| 2005/0192587 A1 | 9/2005 | Lim |
| 2005/0197700 A1 | 9/2005 | Boehm et al. |
| 2005/0197705 A1 | 9/2005 | Arnin et al. |
| 2005/0203511 A1 | 9/2005 | Wilson-MacDonald et al. |
| 2005/0203513 A1 | 9/2005 | Jahng et al. |
| 2005/0203514 A1 | 9/2005 | Jahng et al. |
| 2005/0203517 A1 | 9/2005 | Jahng et al. |
| 2005/0209593 A1 | 9/2005 | Kolb |
| 2005/0209694 A1 | 9/2005 | Loeb |
| 2005/0215999 A1 | 9/2005 | Birkmeyer et al. |
| 2005/0216000 A1 | 9/2005 | Colleran et al. |
| 2005/0222569 A1 | 10/2005 | Panjabi |
| 2005/0228378 A1 | 10/2005 | Kalfas et al. |
| 2005/0228381 A1 | 10/2005 | Kirschman |
| 2005/0234551 A1 | 10/2005 | Fallin et al. |
| 2005/0235508 A1 | 10/2005 | Augostino et al. |
| 2005/0240264 A1 | 10/2005 | Tokish, Jr. et al. |
| 2005/0240265 A1 | 10/2005 | Kuioer et al. |
| 2005/0245928 A1 | 11/2005 | Colleran et al. |
| 2005/0245930 A1 | 11/2005 | Timm et al. |
| 2005/0249697 A1 | 11/2005 | Ulrich et al. |
| 2005/0261682 A1 | 11/2005 | Ferree |
| 2005/0261768 A1 | 11/2005 | Trieu |
| 2005/0273167 A1 | 12/2005 | Triolett et al. |
| 2005/0277921 A1 | 12/2005 | Eisermann et al. |
| 2005/0277922 A1 | 12/2005 | Trieu et al. |
| 2005/0288670 A1 | 12/2005 | Panjabi et al. |
| 2006/0004449 A1 | 1/2006 | Goble et al. |
| 2006/0004451 A1 | 1/2006 | Goble et al. |
| 2006/0015100 A1 | 1/2006 | Paniabi et al. |
| 2006/0025769 A1 | 2/2006 | Dick et al. |
| 2006/0036240 A1 | 2/2006 | Colleran et al. |
| 2006/0036244 A1 | 2/2006 | Soitler et al. |
| 2006/0036255 A1 | 2/2006 | Pond, Jr. et al. |
| 2006/0036260 A1 | 2/2006 | Runco et al. |
| 2006/0052785 A1 | 3/2006 | Augostino et al. |
| 2006/0058791 A1 | 3/2006 | Broman et al. |
| 2006/0069391 A1 | 3/2006 | Jackson |
| 2006/0079894 A1 | 4/2006 | Colleran et al. |
| 2006/0079909 A1 | 4/2006 | Runco et al. |
| 2006/0084976 A1 | 4/2006 | Borgstrom et al. |
| 2006/0084982 A1 | 4/2006 | Kim |
| 2006/0084984 A1 | 4/2006 | Kim |
| 2006/0084987 A1 | 4/2006 | Kim |
| 2006/0084991 A1 | 4/2006 | Borgstrom et al. |
| 2006/0085072 A1 | 4/2006 | Funk et al. |
| 2006/0106380 A1 | 5/2006 | Colleran |
| 2006/0106394 A1 | 5/2006 | Colleran |
| 2006/0111713 A1 | 5/2006 | Jackson |
| 2006/0142759 A1 | 6/2006 | Arnin et al. |
| 2006/0142761 A1 | 6/2006 | Landry et al. |
| 2006/0149238 A1 | 7/2006 | Sherman et al. |
| 2006/0149239 A1 | 7/2006 | Winslow et al. |
| 2006/0149254 A1 | 7/2006 | Lauryssen et al. |
| 2006/0149272 A1 | 7/2006 | Winslow et al. |
| 2006/0149289 A1 | 7/2006 | Winslow et al. |
| 2006/0149373 A1 | 7/2006 | Winslow et al. |
| 2006/0149374 A1 | 7/2006 | Winslow et al. |
| 2006/0149375 A1 | 7/2006 | Yuan et al. |
| 2006/0149383 A1 | 7/2006 | Arnin et al. |
| 2006/0173454 A1 | 8/2006 | Spitler et al. |
| 2006/0189983 A1 | 8/2006 | Fallin et al. |
| 2006/0189984 A1 | 8/2006 | Fallin et al. |
| 2006/0190083 A1 | 8/2006 | Arnin et al. |
| 2006/0195086 A1 | 8/2006 | Sybert |
| 2006/0200137 A1 | 9/2006 | Soboleski et al. |
| 2006/0217718 A1 | 9/2006 | Chervitz et al. |
| 2006/0217719 A1 | 9/2006 | Albert et al. |
| 2006/0229616 A1 | 10/2006 | Albert et al. |
| 2006/0235388 A1 | 10/2006 | Justis et al. |
| 2006/0235393 A1 | 10/2006 | Bono et al. |
| 2006/0235414 A1 | 10/2006 | Lim et al. |
| 2006/0241593 A1 | 10/2006 | Sherman et al. |
| 2006/0241595 A1 | 10/2006 | Molz, IV et al. |
| 2006/0241597 A1 | 10/2006 | Mitchell et al. |
| 2006/0241599 A1 | 10/2006 | Konieczynski et al. |
| 2006/0241642 A1 | 10/2006 | Amin et al. |
| 2006/0241758 A1 | 10/2006 | Peterman et al. |
| 2006/0241759 A1 | 10/2006 | Trieu |
| 2006/0241768 A1 | 10/2006 | Trieu |
| 2006/0241769 A1 | 10/2006 | Gordon et al. |
| 2006/0247623 A1 | 11/2006 | Anderson et al. |
| 2006/0247628 A1 | 11/2006 | Rawlins et al. |
| 2006/0247630 A1 | 11/2006 | Iott et al. |
| 2006/0247632 A1 | 11/2006 | Winslow et al. |
| 2006/0247633 A1 | 11/2006 | Winslow et al. |
| 2006/0247637 A1 | 11/2006 | Colleran et al. |
| 2006/0247649 A1 | 11/2006 | Rezach et al. |
| 2006/0247650 A1 | 11/2006 | Yerby et al. |
| 2006/0247658 A1 | 11/2006 | Pond, Jr. et al. |
| 2006/0247769 A1 | 11/2006 | Molz et al. |
| 2006/0247773 A1 | 11/2006 | Stamp |
| 2006/0260483 A1 | 11/2006 | Hartmann et al. |
| 2006/0264934 A1 | 11/2006 | Fallin |
| 2006/0264962 A1 | 11/2006 | Chin et al. |
| 2006/0265069 A1 | 11/2006 | Goble et al. |
| 2006/0271198 A1 | 11/2006 | McAfee |
| 2006/0276798 A1 | 12/2006 | Lim |
| 2006/0276801 A1 | 12/2006 | Yerby et al. |
| 2006/0276897 A1 | 12/2006 | Winslow et al. |
| 2006/0282075 A1 | 12/2006 | Labrom et al. |
| 2006/0282077 A1 | 12/2006 | Labrom et al. |
| 2006/0282078 A1 | 12/2006 | Labrom et al. |
| 2006/0282079 A1 | 12/2006 | Labrom et al. |

| | | |
|---|---|---|
| 2006/0282080 A1 | 12/2006 | Albert et al. |
| 2006/0293657 A1 | 12/2006 | Hartmann |
| 2006/0293690 A1 | 12/2006 | Abdelgany |
| 2006/0293692 A1 | 12/2006 | Whipple et al. |
| 2007/0005062 A1 | 1/2007 | Lanoe et al. |
| 2007/0005063 A1 | 1/2007 | Bruneau et al. |
| 2007/0016191 A1 | 1/2007 | Culbert et al. |
| 2007/0016193 A1 | 1/2007 | Ritland |
| 2007/0016195 A1 | 1/2007 | Winslow et al. |
| 2007/0016196 A1 | 1/2007 | Winslow et al. |
| 2007/0016218 A1 | 1/2007 | Winslow et al. |
| 2007/0016296 A1 | 1/2007 | Triplett et al. |
| 2007/0043358 A1 | 2/2007 | Molz, IV et al. |
| 2007/0043359 A1 | 2/2007 | Altarac |
| 2007/0049931 A1 | 3/2007 | Justis et al. |
| 2007/0055242 A1 | 3/2007 | Bailly |
| 2007/0055257 A1 | 3/2007 | Vaccaro et al. |
| 2007/0073289 A1 | 3/2007 | Kwak et al. |
| 2007/0073396 A1 | 3/2007 | Arnin |
| 2007/0083264 A1 | 4/2007 | Arnin et al. |
| 2007/0090238 A1 | 4/2007 | Justis |
| 2007/0093816 A1 | 4/2007 | Arnin et al. |
| 2007/0100341 A1 | 5/2007 | Reqlos et al. |
| 2007/0118120 A1 | 5/2007 | A. Farris et al. |
| 2007/0118132 A1 | 5/2007 | Culbert et al. |
| 2007/0123861 A1 | 5/2007 | Dewey et al. |
| 2007/0123863 A1 | 5/2007 | Winslow et al. |
| 2007/0123989 A1 | 5/2007 | Gfeller et al. |
| 2007/0135814 A1 | 6/2007 | Farris |
| 2007/0161998 A1 | 7/2007 | Whipple |
| 2007/0173828 A1 | 7/2007 | Firkins et al. |
| 2007/0213722 A1 | 9/2007 | Jones et al. |
| 2007/0219556 A1 | 9/2007 | Altarac et al. |
| 2007/0225712 A1 | 9/2007 | Altarac et al. |
| 2007/0225713 A1 | 9/2007 | Altarac et al. |
| 2007/0233079 A1 | 10/2007 | Fallin et al. |
| 2007/0239159 A1 | 10/2007 | Altarac et al. |
| 2007/0255284 A1 | 11/2007 | Miller et al. |
| 2007/0270811 A1 | 11/2007 | Dewey |
| 2007/0270867 A1 | 11/2007 | Miller et al. |
| 2007/0270868 A1 | 11/2007 | Dewey |
| 2007/0270869 A1 | 11/2007 | Young et al. |
| 2007/0276379 A1 | 11/2007 | Miller et al. |
| 2008/0009864 A1 | 1/2008 | Forton et al. |
| 2008/0015601 A1 | 1/2008 | Castro et al. |
| 2008/0039839 A1 | 2/2008 | Songer et al. |
| 2008/0045957 A1 | 2/2008 | Landry et al. |
| 2008/0051787 A1 | 2/2008 | Reminton et al. |
| 2008/0065072 A1 | 3/2008 | Spitler et al. |
| 2008/0077136 A1 | 3/2008 | Triplett et al. |
| 2008/0077139 A1 | 3/2008 | Landry et al. |
| 2008/0077155 A1 | 3/2008 | Diederich et al. |
| 2008/0097441 A1 | 4/2008 | Hayes et al. |
| 2008/0177275 A1 | 7/2008 | Wing et al. |
| 2008/0183215 A1 | 7/2008 | Altarac et al. |
| 2008/0221626 A1 | 9/2008 | Butiers et al. |
| 2008/0228233 A1 | 9/2008 | Hoffman et al. |
| 2008/0234678 A1 | 9/2008 | Gutierrez et al. |
| 2008/0234765 A1 | 9/2008 | Frasier et al. |
| 2008/0243126 A1 | 10/2008 | Gutierrez et al. |
| 2008/0249372 A1 | 10/2008 | Reglos et al. |
| 2008/0249628 A1 | 10/2008 | Altarac et al. |
| 2008/0262554 A1 | 10/2008 | Hayes et al. |
| 2008/0306488 A1 | 12/2008 | Altarac et al. |
| 2008/0306489 A1 | 12/2008 | Altarac et al. |
| 2008/0306557 A1 | 12/2008 | Altarac et al. |
| 2008/0312692 A1 | 12/2008 | Brennan et al. |
| 2009/0030465 A1 | 1/2009 | Altarac et al. |
| 2009/0036929 A1 | 2/2009 | Reglos et al. |
| 2009/0082775 A1 | 3/2009 | Altarac et al. |
| 2009/0125032 A1 | 5/2009 | Gutierrez et al. |
| 2009/0125047 A1 | 5/2009 | Reglos et al. |
| 2009/0138056 A1 | 5/2009 | Anderson et al. |
| 2009/0177196 A1 | 7/2009 | Zlock et al. |
| 2009/0204155 A1* | 8/2009 | Aschmann .................. 606/264 |
| 2009/0216237 A1 | 8/2009 | Frezal et al. |
| 2009/0228045 A1 | 9/2009 | Hayes et al. |
| 2009/0228053 A1 | 9/2009 | Kolb et al. |
| 2009/0228054 A1 | 9/2009 | Hoffman et al. |
| 2009/0228055 A1 | 9/2009 | Jackson |
| 2010/0036423 A1 | 2/2010 | Hayes et al. |
| 2010/0174317 A1 | 7/2010 | Timm et al. |
| 2010/0222819 A1 | 9/2010 | Timm et al. |
| 2011/0144701 A1 | 6/2011 | Altarac et al. |
| 2011/0166610 A1 | 7/2011 | Altarac et al. |

FOREIGN PATENT DOCUMENTS

| | | |
|---|---|---|
| EP | 0986339 | 3/2000 |
| EP | 951246 | 7/2001 |
| EP | 1138268 | 10/2001 |
| EP | 1145602 | 10/2001 |
| EP | 1056408 | 12/2003 |
| EP | 1303225 | 5/2005 |
| EP | 1399078 | 5/2005 |
| EP | 1415602 | 7/2005 |
| EP | 1415603 | 7/2005 |
| EP | 1128773 B1 | 6/2006 |
| EP | 1459690 B1 | 6/2006 |
| EP | 986338 B1 | 7/2006 |
| EP | 1810624 | 7/2007 |
| FR | 2728454 | 6/1996 |
| WO | WO-9116018 | 10/1991 |
| WO | WO-9426192 | 11/1994 |
| WO | 9531158 | 11/1995 |
| WO | WO-9600049 | 1/1996 |
| WO | WO-9822033 | 5/1998 |
| WO | WO-9848717 | 11/1998 |
| WO | WO-9848717 A1 | 11/1998 |
| WO | WO-9855038 | 12/1998 |
| WO | WO-0062684 | 10/2000 |
| WO | WO-0130248 | 5/2001 |
| WO | WO-0141681 | 6/2001 |
| WO | 0238060 | 5/2002 |
| WO | WO-02065954 | 8/2002 |
| WO | 02067793 | 9/2002 |
| WO | WO-02102259 | 12/2002 |
| WO | WO-03047442 | 6/2003 |
| WO | WO-03075805 | 9/2003 |
| WO | WO-03094699 | 11/2003 |
| WO | WO-03094699 A2 | 11/2003 |
| WO | WO-03101350 | 12/2003 |
| WO | WO-2004008949 A3 | 1/2004 |
| WO | 2004078221 | 9/2004 |
| WO | WO-2004047617 B1 | 11/2004 |
| WO | WO-2004103227 | 12/2004 |
| WO | WO-2004103228 | 12/2004 |
| WO | WO-2005009301 | 2/2005 |
| WO | WO-2005013864 | 2/2005 |
| WO | WO-2005018471 A1 | 3/2005 |
| WO | 2005030029 | 4/2005 |
| WO | 2005030031 | 4/2005 |
| WO | WO-2005030066 | 4/2005 |
| WO | WO-2005030067 | 4/2005 |
| WO | WO-2005030087 | 4/2005 |
| WO | 2005041799 | 5/2005 |
| WO | WO-2005044152 | 5/2005 |
| WO | WO-2005046515 | 5/2005 |
| WO | 2005055874 | 6/2005 |
| WO | WO-2005053572 | 6/2005 |
| WO | WO-2005060879 | 7/2005 |
| WO | WO-2005067824 | 7/2005 |
| WO | WO-2005070278 | 8/2005 |
| WO | WO-2005070349 | 8/2005 |
| WO | WO-2005070350 | 8/2005 |
| WO | WO-2005070351 | 8/2005 |
| WO | WO-2005070352 | 8/2005 |
| WO | WO-2005070353 | 8/2005 |
| WO | WO-2005070354 | 8/2005 |
| WO | WO-2005076974 | 8/2005 |
| WO | WO-2005077113 | 8/2005 |
| WO | 2005079672 | 9/2005 |
| WO | 2005084590 | 9/2005 |
| WO | 2005087121 | 9/2005 |
| WO | WO-2005079426 | 9/2005 |
| WO | WO-2005079711 | 9/2005 |
| WO | 2005092223 | 10/2005 |
| WO | 2005094704 | 10/2005 |
| WO | WO-2005096974 A3 | 10/2005 |

| | | | |
|---|---|---|---|
| WO | WO-2005104998 A3 | 11/2005 |
| WO | WO-2005117765 | 12/2005 |
| WO | WO-2005120401 | 12/2005 |
| WO | 2006016371 | 2/2006 |
| WO | 2006017507 | 2/2006 |
| WO | WO-2006023683 | 3/2006 |
| WO | WO-2006033659 | 3/2006 |
| WO | 2006042188 | 4/2006 |
| WO | 2006042189 | 4/2006 |
| WO | WO-2006039260 A2 | 4/2006 |
| WO | WO-2006023671 | 5/2006 |
| WO | WO-2006047363 | 5/2006 |
| WO | 2006063107 | 6/2006 |
| WO | WO-2006063083 A1 | 6/2006 |
| WO | WO-2006065774 | 6/2006 |
| WO | WO-2006067790 | 6/2006 |
| WO | WO-2006045091 C2 | 8/2006 |
| WO | WO-2006055186 C1 | 8/2006 |
| WO | WO-2006089237 A1 | 8/2006 |
| WO | WO-2006096351 A1 | 9/2006 |
| WO | WO-2006096381 A3 | 9/2006 |
| WO | WO-2006101655 | 9/2006 |
| WO | WO-2006102268 | 9/2006 |
| WO | WO-2006102443 | 9/2006 |
| WO | 2006108067 | 10/2006 |
| WO | WO-2006104999 | 10/2006 |
| WO | WO-2006109310 A1 | 10/2006 |
| WO | WO-2006110796 A1 | 10/2006 |
| WO | WO-2006113256 A2 | 10/2006 |
| WO | 2006125142 | 11/2006 |
| WO | WO-2006115954 A3 | 11/2006 |
| WO | WO-2006116214 | 11/2006 |
| WO | WO-2006119151 A1 | 11/2006 |
| WO | WO-2006119236 A2 | 11/2006 |
| WO | WO-2006119237 A3 | 11/2006 |
| WO | WO-2006119241 A2 | 11/2006 |
| WO | WO-2006135511 | 12/2006 |
| WO | 2007014119 | 2/2007 |
| WO | 2007021588 | 2/2007 |
| WO | WO-2007031998 A2 | 3/2007 |
| WO | WO-2007034472 A1 | 3/2007 |
| WO | WO-2007037801 A2 | 4/2007 |
| WO | WO-2007038261 A1 | 4/2007 |
| WO | WO-2007043044 A1 | 4/2007 |
| WO | 2007075375 | 7/2007 |
| WO | 2007102846 | 9/2007 |
| WO | 2007117366 | 10/2007 |
| WO | 2007121061 | 10/2007 |
| WO | 2007127608 | 11/2007 |
| WO | 2007127682 | 11/2007 |
| WO | 2007136612 | 11/2007 |
| WO | 2008069835 | 6/2008 |
| WO | 2008115549 | 9/2008 |
| WO | 2008121421 | 10/2008 |
| WO | 2008124186 | 10/2008 |
| WO | 2008140756 | 11/2008 |
| WO | 2008153747 | 12/2008 |
| WO | 2009042489 | 4/2009 |
| WO | 2009049206 | 4/2009 |
| WO | 2009076239 | 6/2009 |
| WO | 2009091960 | 7/2009 |
| WO | 2009100190 | 8/2009 |
| WO | 2008121343 | 10/2009 |
| WO | 2010019791 | 2/2010 |
| WO | 2011017712 | 2/2011 |
| WO | 2011028575 | 3/2011 |

OTHER PUBLICATIONS

Co-pending U.S. Appl. No. 11/586,849.
USPTO Final Office Action for U.S. Appl. No. 11/586,849, mailed Jan. 6, 2012.
USPTO Final Office Action for U.S. Appl. No. 12/355,093, mailed Dec. 13, 2011.
USPTO Non-Final Office Action for U.S. Appl. No. 12/270,505, mailed Feb. 16, 2012.
USPTO Communicaiton for U.S. Appl. No. 11/362,366 mailed Apr. 23, 2010.
USPTO Communicaiton for U.S. Appl. No. 11/362,366 mailed Apr. 7, 2009.
First Examiner's Report for AU App. No. 2006272755 mailed May 31, 2011. (pp. 1-3).
Second Exmainer's Report for AU App. No. 2005295209 mailed Jun. 1, 2011. (pp. 1-3).
International Preliminary Report on Patentability and Written Opinion for PCT/US2008/004098, mailed Jul. 25, 2008. (pp. 1-7).
International Preliminary Report on Patentability and Written Opinion for PCT/US2008/03677, mailed Jul. 22, 2008. (pp. 1-9).
International Preliminary Report on Patentability and Written Opinion for PCT/US2008/079580, mailed Apr. 29, 2009. (pp. 1-6).
International Preliminary Report on Patentability and Written Opinion for PCT/US2009/053740, Feb. 21, 2011. (6 pages).
International Search Report and Written Opinion for PCT/US2006/28586, mailed Jul. 27, 2007. (pp. 1-14).
International Search Report and Written Opinion for PCT/US2005/038021, mailed Apr. 10, 2006 (pp. 1-6).
International Search Report and Written Opinion for PCT/US2007/004726, mailed Jul. 8, 2008. (pp. 1-6).
International Search Report and Written Opinion for PCT/US2007/11573, mailed Apr. 23, 2008. (pp. 1-6).
International Search Report and Written Opinion for PCT/US2008/085748, mailed Jun. 22, 2009. (pp. 1-10).
International Search Report and Written Opinion for PCT/US2009/031225, mailed Aug. 31, 2009. (15 pages).
International Search Report for PCT/US2008/004098, mailed Jul. 25, 2008. (1 page).
International Search Report for PCT/US2008/03677, mailed Jul. 22, 2008. (1 page).
International Search Report for PCT/US2008/079580, mailed Apr. 29, 2009. (pp. 1-5).
International Search Report for PCT/US2009/053740, mailed Mar. 24, 2010. (pp. 1-4).
International Search Report for PCT/US2010/44930, mailed Apr. 1, 2011. (pp. 1-4).
Written Opinion for PCT/US2010/44930, mailed Mar. 31, 2009. (pp. 1-4).
USPTO Communicaiton for U.S. Appl. No. 10/970,366 mailed Nov. 25, 2008.
USPTO Communicaiton for U.S. Appl. No. 10/970,366 mailed Nov. 5, 2009.
USPTO Communicaiton for U.S. Appl. No. 11/006,495 mailed Dec. 29, 2009.
USPTO Communicaiton for U.S. Appl. No. 11/006,495 mailed Jun. 6, 2008.
USPTO Communicaiton for U.S. Appl. No. 11/006,495 mailed Mar. 20, 2009.
USPTO Communicaiton for U.S. Appl. No. 11/033,452 mailed Dec. 11, 2008.
USPTO Communicaiton for U.S. Appl. No. 11/033,452 mailed Oct. 13, 2009.
USPTO Communicaiton for U.S. Appl. No. 11/427,738 mailed Dec. 29, 2009.
USPTO Communicaiton for U.S. Appl. No. 11/436,407 mailed Jun. 21, 2009.
USPTO Communication for U.S. Appl. No. 11/006,495 mailed Jun. 30, 2008.
Co-Pending U.S. Appl. No. 11/586,849 by Altarac et al entitled "Systems and methods for stabilization of bone structures" filed Oct. 25, 2006.
USPTO Communicaiton for U.S. Appl. No. 11/586,849, mailed Jul. 8, 2011.
Co-pending U.S. Appl. No. 11/362,366 by Altarac et al. entitled "Systems and methods for stabilization of bone structures" filed Feb. 23, 2006.
Co-Pending U.S. Appl. No. 12/853,260 by Altarac et al entitled "Systems and Methods for Stabilization of Bone Structures, Including Thorocolumbar Stabilization Systems and Methods " filed Aug. 9, 2010.
Co-Pending U.S. Appl. No. 12/270,505 by Gutierrez et al entitled "Rod removal instrument" filed Nov. 13, 2008.

Co-Pending U.S. Appl. No. 12/355,093 by Reglos et al entitled "Tissue splitter" filed Jan. 16, 2009.
USPTO Communication for U.S. Appl. No. 12/355,093, mailed Jun. 27, 2011.
Co-Pending U.S. Appl. No. 12/966,807 by Altarac et al entitled "Methods for Stabilization of Bone Structures" filed Dec. 13, 2010.
Co-Pending U.S. Appl. No. 12/966,790 by Altarac et al entitled "Method for Stabilizing Bone Strucutres" filed Dec. 13, 2010.
Co-Pending U.S. Appl. No. 12/077,462 by Gutierrez et al entitled "Rod reducer" filed Mar. 19, 2008.
USPTO Communication for U.S. Appl. No. 12/077,462, mailed Mar. 18, 2011.
Co-Pending U.S. Appl. No. 12/329,423 by Altarac et al entitled "Spondylolisthesis reduction system and method" filed Dec. 5, 2008.
USPTO Advisory Action for U.S. Appl. No. 11/726,093, mailed Aug. 30, 2011.
USPTO Notice of Allowance for U.S. Appl. No. 12/077,462, mailed Sep. 28, 2011.
USPTO Final Office Action for U.S. Appl. No. 11/362,366 mailed Oct. 27, 2011.
USPTO Non-Final Office Action for U.S. Appl. No. 12/329,423, mailed Nov. 30, 2011.
USPTO Non-Final Office Action for U.S. Appl. No. 11/362,366 mailed Mar. 18, 2011.
First Examiner's Report for Australian App. No. 2008229323 mailed Jun. 24, 2012. (pp. 4).
Extended European Search Report for European Patent Application No. 08742359.6, mailed Jun. 27, 2012. (5 pages).
USPTO Notice of Allowance for U.S. Appl. No. 11/726,093, mailed May 10, 2012. (available in USPTO PAIR).
USPTO Final Office Action for U.S. Appl. No. 12/270,505, mailed Jul. 19, 2012. (available in USPTO PAIR).
USPTO Non-Final Office Action for U.S. Appl. No. 12/853,260, mailed Jul. 13, 2012, (available in USPTO PAIR).

* cited by examiner

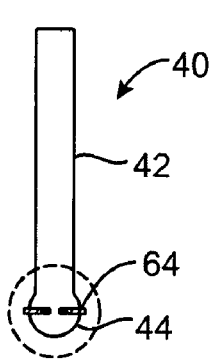
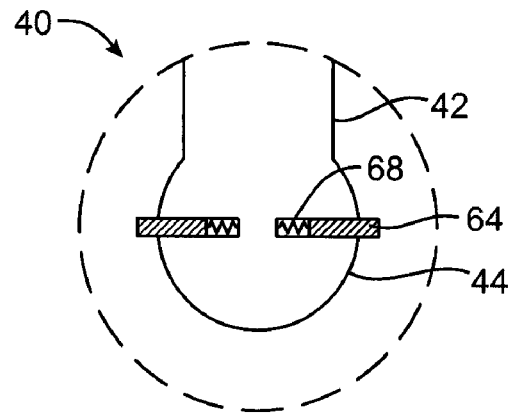
FIG. 3          FIG. 3A
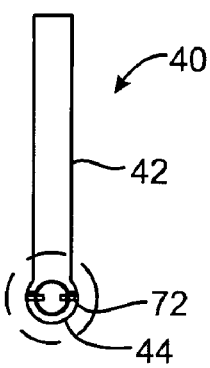
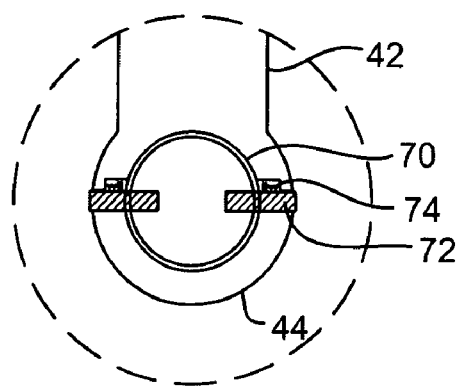
FIG. 4          FIG. 4A
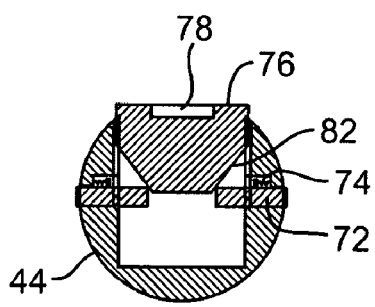
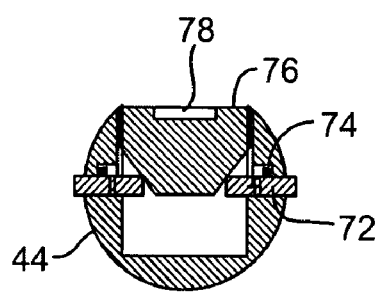
FIG. 4B         FIG. 4C

US 8,267,969 B2

SCREW SYSTEMS AND METHODS FOR USE IN STABILIZATION OF BONE STRUCTURES

CROSS REFERENCE TO RELATED APPLICATIONS

This application is a continuation-in-part of U.S. patent application Ser. No. 11/427,738 entitled "Systems and methods for posterior dynamic stabilization of the spine" filed on Jun. 29, 2006, which is a continuation-in-part of U.S. patent application Ser. No. 11/436,407 filed on May 17, 2006, which is a continuation-in-part of U.S. patent application Ser. No. 11/033,452 filed on Jan. 10, 2005, which is a continuation-in-part of U.S. patent application Ser. No. 11/006,495 filed on Dec. 6, 2004, which is a continuation-in-part of U.S. patent application Ser. No. 10/970,366 filed on Oct. 20, 2004; U.S. patent application Ser. No. 11/427,738 is also a continuation-in-part of U.S. patent application Ser. No. 11/362,366 filed on Feb. 23, 2006, which is a continuation-in-part of U.S. Patent Application Ser. No. 60/701,660 filed on Jul. 22, 2005, all of which are incorporated herein by reference in their entirety. This application is also a continuation-in-part of U.S. patent application Ser. No. 11/586,849 entitled "Systems and methods for stabilization of bone structures" filed on Oct. 25, 2006, which is a continuation-in-part of U.S. patent application Ser. No. 11/362,366 filed on Feb. 23, 2006, which is a continuation-in-part of U.S. Patent Application Ser. No. 60/701,660 filed on Jul. 22, 2005, all of which are incorporated herein by reference in their entirety.

FIELD

The present invention generally relates to surgical instruments and methods for using these instruments. More particularly, but not exclusively, minimally invasive methods of stabilizing one or more bone structures are disclosed.

BACKGROUND

Systems, methods and devices for stabilizing one or more bone structures of a patient have been available for many years. Prior art procedures typically require large incisions and also significant tissue manipulation to adequately expose the areas intended for the attachment. The procedures are associated with long recovery times and increased potential for adverse events, such as infection, usually associated with muscle and other tissue trauma and scarring.

Currently available minimally invasive techniques and products are limited. These procedures are difficult to perform, especially in spinal applications in which the attachment points are deeper in tissue, and damage to neighboring tissue must be avoided. Many of the currently available less invasive products remain somewhat invasive due to component configurations, and required manipulations to be performed during the attachment.

In reference specifically to treatment of the spine, FIGS. 1A-1B illustrate a portion of the human spine having a superior vertebra 2 and an inferior vertebra 4, with an intervertebral disc 6 located in between the two vertebral bodies. The superior vertebra 2 has superior facet joints 8a and 8b, inferior facet joints 10a and 10b, posterior arch 16 and spinous process 18. Pedicles 3a and 3b interconnect the respective superior facet joints 8a, 8b to the vertebral body 2. Extending laterally from superior facet joints 8a, 8b are transverse processes 7a and 7b, respectively. Extending between each inferior facet joints 10a and 10b and the spinous process 18 are lamina 5a and 5b, respectively. Similarly, inferior vertebra 4 has superior facet joints 12a and 12b, superior pedicles 9a and 9b, transverse processes 11a and 11b, inferior facet joints 14a and 14b, lamina 15a and 15b, posterior arch 20, spinous process 22.

The superior vertebra with its inferior facets, the inferior vertebra with its superior facets, the intervertebral disc, and seven spinal ligaments (not shown) extending between the superior and inferior vertebrae together comprise a spinal motion segment or functional spine unit. Each spinal motion segment enables motion along three orthogonal axis, both in rotation and in translation. The various spinal motions are illustrated in FIGS. 1C-1D. In particular, FIG. 1C illustrates flexion and extension motions, anterior translation, and axial loading, FIG. 1D illustrates lateral bending motion and lateral translation motion. A normally functioning spinal motion segment provides physiological limits and stiffness in each rotational and translational direction to create a stable and strong column structure to support physiological loads.

Various disorders of the spine can produce debilitating pain that can affect a spinal-motion segment's ability to properly function. The specific location or source of spinal pain is most often an affected intervertebral disc or facet joint. Often, a disorder in one location or spinal component can lead to eventual deterioration or disorder, and ultimately, pain in the other.

Spine fusion (arthrodesis) is a procedure in which two or more adjacent vertebral bodies are fused together. While spine fusion generally helps to eliminate certain types of pain, it has been shown to decrease function by limiting the range of motion for patients in flexion, extension, rotation and lateral bending. Furthermore, the fusion creates increased stresses on adjacent non-fused motion segments and accelerated degeneration of the motion segments.

Various technologies and approaches have been developed to treat spinal pain without fusion in order to maintain or recreate the natural biomechanics of the spine. To this end, significant efforts are being made in the use of implantable artificial intervertebral discs. Unfortunately, the currently available artificial discs do not adequately address all of the mechanics of motion for the spinal column.

It has been found that the facet joints can also be a significant source of spinal disorders and debilitating pain. Current interventions for the treatment of facet joint disorders have not been found to provide completely successful results.

Most recently, surgical-based technologies, referred to as "dynamic posterior stabilization," have been developed to address spinal pain resulting from more than one disorder, when more than one structure of the spine have been compromised. An objective of such technologies is to provide the support of fusion-based implants while maximizing the natural biomechanics of the spine. Dynamic posterior stabilization systems typically fall into one of two general categories: (1) interspinous spacers and (2) posterior pedicle screw-based systems.

Examples of interspinous spacers are disclosed in U.S. Pat. Nos. Re. 36,211, 5,645,599, 6,695,842, 6,716,245 and 6,761,720.

Examples of pedicle screw-based systems are disclosed in U.S. Pat. Nos. 5,015,247, 5,484,437, 5,489,308, 5,609,636 and 5,658,337, 5,741,253, 6,080,155, 6,096,038, 6,264,656 and 6,270,498. These types of systems involve the use of screws which are positioned in the vertebral body through the pedicle. Certain types of these pedicle screw-based systems may be used to augment compromised facet joints, while others require removal of the spinous process and/or the facet joints for implantation. One such system, employs a cord which is extended between the pedicle screws and a fairly rigid spacer which is passed over the cord and positioned between the screws. While this system is able to provide load sharing and restoration of disc height, because it is so rigid, it is not effective in preserving the natural motion of the spinal segment into which it is implanted. Other pedicle screw-based systems employ joints between the pedicle screws that provide some discreet amounts of movement in different directions to somewhat simulate the complex movement of the spine.

There remains a need for minimally invasive methods and devices for bone stabilization procedures, including but not limited to spinal segment stabilization procedures such as dynamic spinal segment stabilization procedures Furthermore, there is an ongoing need for systems that provide easier insertion for the clinician. Systems that allow simplified multiple degree of freedom of adjustment during implantation that then can be securely fixed are needed as are systems that can reduce fatigue failures, avoid large stresses between components under all load conditions and generally have a long implant life.

SUMMARY

According to one aspect of the invention, a bone screw system is provided. The bone screw includes a threaded section and a screw head section integrally connected to the threaded section. The system includes a coupler having a screw head receiving portion configured to receive at least a portion of the screw head section of the screw. The coupler also includes a rod receiving portion integral with the screw head receiving portion. The rod receiving portion is configured to receive a rod. The system includes a seat having a first end and a second end. The seat further includes at least one sidewall extending between the first end and the second end, a cap receiving portion configured to receive a cap at the first end and a coupler receiving portion configured to receive the coupler. The seat includes a bottom opening at the second end and a top opening at the first end. At least one rod channel defined by the sidewall and the at least one rod channel is interconnected with the top opening. The system includes a cap configured to close the top opening of the seat. The cap has a top surface and a bottom surface interconnected by an outer surface and an inner surface. The inner surface defines a threaded set screw receiving portion and the outer surface defines at least one seat-engagement feature for engagement with the cap receiving portion of the seat. The system includes a set screw having a top surface and a bottom surface interconnected by a threaded outer surface. The set screw is configured to be threadingly engaged with the set screw receiving portion of the cap. The system further includes a retainer configured to retain the coupler inside the seat. A rod is provided. The rod has a first end and a second end. The first end of the rod is configured to connect to the rod receiving portion of the coupler. At least a portion of the screw head section is disposed inside the screw head receiving portion of the coupler. The screw is inserted in the bottom opening of the seat and the coupler is retained inside the seat via the retainer pressed between the coupler and the seat. The first end of the rod is removably connected to the rod receiving portion of the coupler. The cap is removably inserted into the cap receiving portion of the seat and retained therein via the at least one seat-engagement feature on the outer surface of the cap. The set screw is disposed in the set screw receiving portion of the cap. The rod is disposed in the rod channel with the cap disposed in the cap receiving portion of the seat. Upon advancement of the screw, the bottom surface of the set screw contacts at least a portion of the rod within the seat and the bone screw and rod is locked into position with advancement of the set screw into the seat.

According to another aspect of the invention, a bone screw system having a locked configuration and an unlocked configuration is provided. The bone screw system includes a rod and a seat. The seat has a first end and a second end and is configured to receive at least a portion of the rod inside the seat such that the rod has a range of motion relative to the seat while in the unlocked configuration. A bone screw having a first end and a second end is also provided. At least a portion of the first end of the bone screw is disposed inside the seat. The screw has a range of motion relative to the seat when in the unlocked configuration. A lock down mechanism is removably disposed inside the seat at the first end of the seat. At least a portion of the rod is located between the lock down mechanism and the first end of the screw. The lock down mechanism is operable between a locked configuration and an unlocked configuration such that both the rod or the screw is locked into position as the lock down mechanism operates from the unlocked configuration to the locked configuration.

According to yet another aspect of the invention, a bone screw system is provided. The bone screw system includes a rod and a bone screw having a first end and a second end. The system includes a seat having a bottom opening. Also included is a coupler having a rod receiving portion and a bone screw receiving portion. The rod receiving portion of the coupler is configured to connect to the rod and the bone screw receiving portion is configured to house at least a portion of the first end of the bone screw. At least a portion of the bone screw is retained in the bone screw receiving portion of the coupler which is retained inside the seat such that the bone screw is connected to the seat via the coupler and such that the bone screw extends through the bottom opening of the seat. The rod is connected to the rod receiving portion of the coupler.

According to another aspect of the invention a system for housing at least a portion of a bone screw is provided. The system includes a seat having a first end and a second end, and an inner surface and an outer surface. At least a portion of the bone screw is retained inside the seat. The seat includes a top opening at the first end and a bottom opening at the second end. At least one sidewall extends between the first end and the second end. The seat includes a closure mechanism receiving portion and a screw receiving portion.

According to another aspect of the invention, a method for inserting a screw system is provided. The method includes the step of providing a system that includes a bone screw and a seat. The seat has a first end, a second end, an inner surface and an outer surface. At least a portion of the bone screw is retained inside the seat. The seat includes a top opening at the first end and at least one sidewall extending between the first end and the second end. A flange is formed on the outer surface of the seat such that the flange extends outwardly from the seat; the flange has an upper surface, a lower surface and an outer surface. The method includes the step of providing an instrument having a first portion and a second portion at a distal end of the instrument. The first and second portions are controllable at the instrument's proximal end by a user. The method includes the steps of contacting at least a portion of the lower surface of the flange with the first portion of the instrument and contacting at least a portion of the upper surface of the flange with the second portion of the instrument. The second portion of the instrument is advanced to apply a force on the flange. The force is biased by the first portion of the instrument to secure the instrument to the seat. The system includes the step of delivering the system into the patient with the instrument.

According to another aspect of the invention, a method is provided. The method includes the step of providing a system comprising a seat having a first end and a second end. The seat includes at least one sidewall extending between the first end and the second end and at least one rod channel formed in the sidewall. The seat also has a top opening at the first end. The system includes a coupler retained inside the seat. The coupler has a rod receiving portion and a screw receiving portion. The system further includes a bone screw that is retained inside the screw receiving portion of the coupler. The method includes the steps of delivering the system into a patient and inserting the bone screw into a bone of the patient. The method includes the step of providing a rod having a first end and a second end and delivering the rod into the patient. The first end of the rod is pivotally connected to the rod receiving portion of the coupler. The method includes the step of pivoting the rod into position. A closure mechanism is provided. The closure mechanism is delivered into the patient to close the top opening of the seat.

According to another aspect of the invention, a bone screw system is provided. The system includes a bone screw and a seat having a first end and a second end. The seat retains the bone screw inside the seat. The seat includes at least one sidewall extending between the first end and the second end. The seat has a top opening at the first end and a cap receiving portion in the at least one sidewall. The cap receiving portion is configured to receive a cap within the seat at the first end. The cap receiving portion has at least one wing groove that has an upper surface. The system includes a cap that is configured to close the top opening of the seat. The cap has a top surface and a bottom surface interconnected by an outer surface and an inner surface. The inner surface defines a set screw receiving portion. The outer surface of the cap defines at least one wing lug extending outwardly from the outer surface of the cap. The wing lug is configured to mate with the at least one wing groove of the seat by rotation of the wing lug into the wing groove. The system includes a set screw having a top surface and a bottom surface interconnected by a threaded outer surface. The set screw is configured to be threadingly engaged with the set screw receiving portion of the cap. The set screw is inserted into the set screw receiving portion of the cap. The cap is removably inserted into the cap receiving portion of the seat closing the top opening. With the cap in the seat, the cap is rotated to position the at least one wing lug inside the at least one wing groove. The set screw is advanced into the seat. Set screw advancement is biased by the seat raising the cap such that the at least one wing lug contacts the upper surface of the wing groove, secures the cap to the seat and prevents splaying of the seat sidewall.

Advantages of the invention may include one or more of the following. Insertion of certain of the described screws and pivoting rods may be performed with reduced insertion forces, and may feature simplified usage. Rotational locking may be employed to secure the pivoting rod against movement. Embodiments of the invention allow reduced stress on the pivoting rod. Embodiments of the invention are compatible with other pedicle screw systems and/or spinal implants. Embodiments of the invention may be applicable to patients with degenerative disc disease, spinal stenosis, spondylolisthesis, spinal deformities, fractures, pseudarthrosis, tumors, failed prior fusions, or other vertebral segment trauma and disease.

It is noted that perfect alignment of the screws with one another is quite difficult and requires great skill on the part of the surgeon to accomplish. Alignment of the screws is even more difficult in minimally invasive/percutaneous procedures. Alignment may further be complicated by the patient's condition such as damaged or diseased bone or other anatomical condition. Screws can be out-of-alignment not only in one plane but in two and in some cases three planes. However, the polyaxial seat of the screw of the present invention advantageously allows the seat to swivel on top of the screw such that they may be lined up regardless of the orientation of the screws' axes and can even thus be made to accommodate a certain amount of misalignment from difference in height once they are inserted into bone. The polyaxial motion of the seat allows the rod channels to be lined-up so that the rod can be placed or attached between the screws without having their axes perfectly aligned to do so. Then the seat can be modified to eliminate motion and stabilize one or more vertebral segments.

Other advantages will be apparent from the description that follows, including the drawings and claims.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures:

FIGS. 3 and 3A illustrate top and enlarged top views of a rod attachment mechanism which may be employed in an embodiment of the present invention.

FIGS. 4 and 4A illustrate top and enlarged top views of another rod attachment mechanism which may be employed in an embodiment of the present invention.

FIGS. 4B and 4C illustrate side cross-sectional view of details of a set screw system for use in the system of FIGS. 4 and 4A.

DETAILED DESCRIPTION

Before the subject devices, systems and methods are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs.

It must be noted that as used herein and in the appended claims, the singular forms "a", "an", and "the" include plural referents unless the context clearly dictates otherwise. Thus, for example, reference to "a spinal segment" may include a plurality of such spinal segments and reference to "the screw" includes reference to one or more screws and equivalents thereof known to those skilled in the art, and so forth.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Figure 1A:
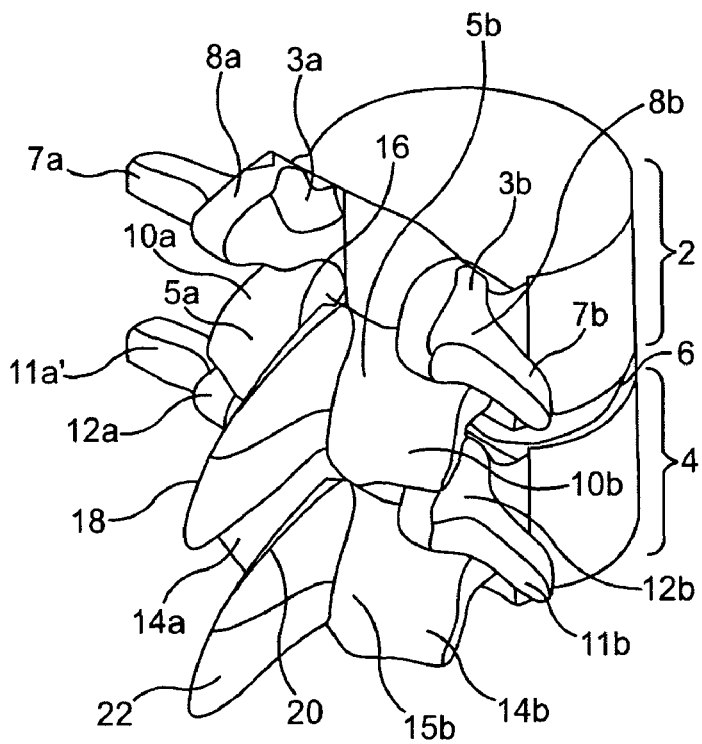
FIGS. 1A and 1B illustrate perspective views of a portion of the human spine having two vertebral segments, where the spinous process and the lamina of the superior vertebra have been resected in FIG. 1B.
Figure 1B:
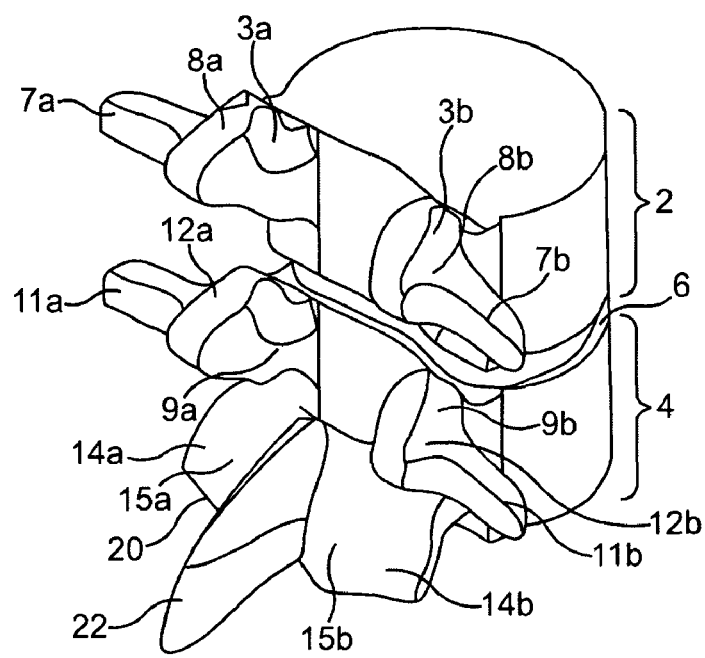
Figure 1C:
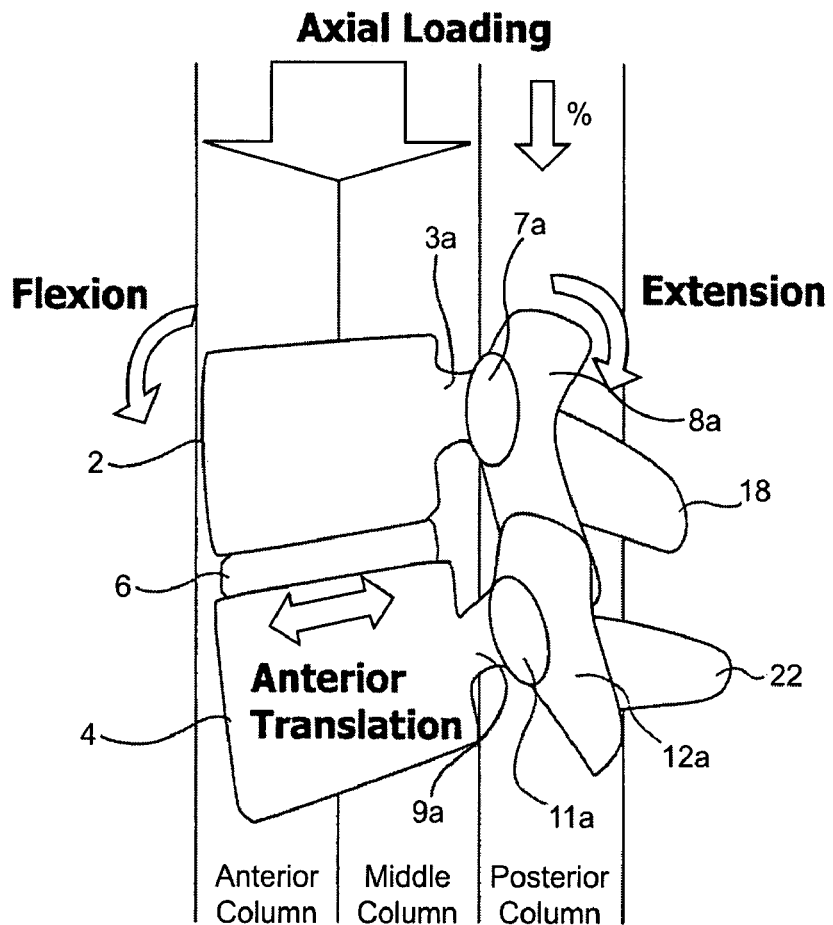
FIGS. 1C, 1D and 1E illustrate left, dorsal and top views, respectively, of the spinal segments of FIG. 1A-1B under going various motions.
Figure 1D:
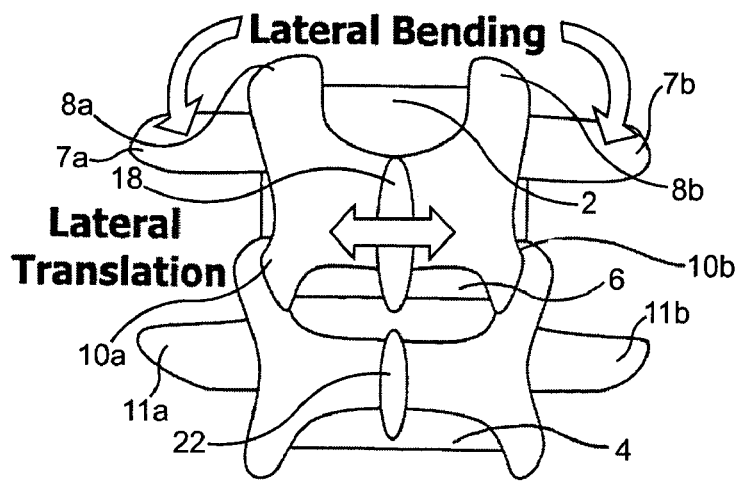
Figure 1E:
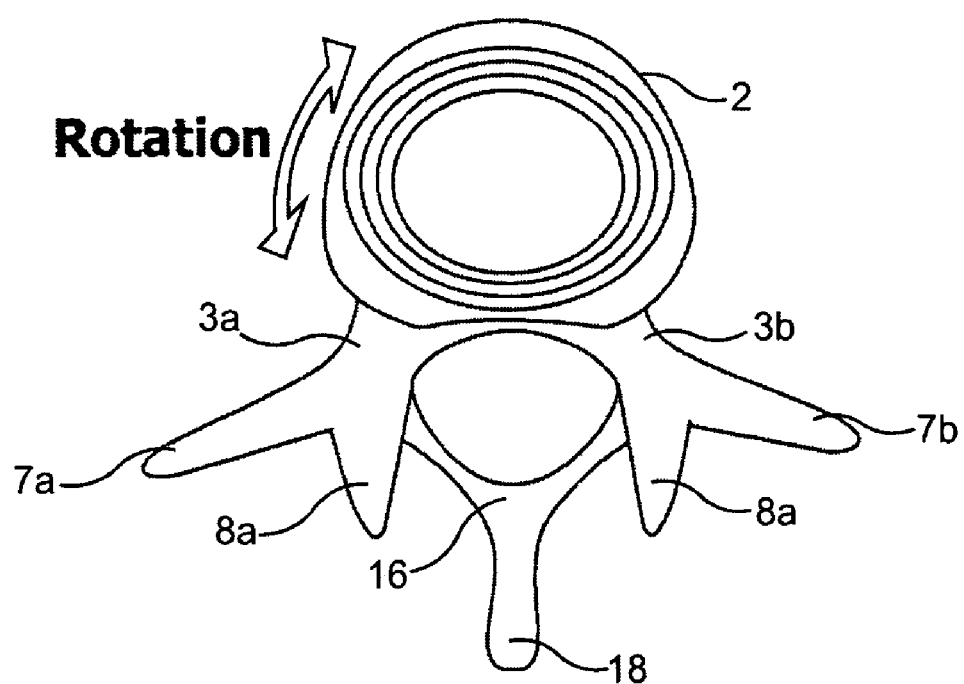

The present invention will now be described in greater detail by way of the following description of exemplary embodiments and variations of the systems and methods of the present invention. While more fully described in the context of the description of the subject methods of implanting the subject systems, it should be initially noted that in certain applications where the natural facet joints are compromised, inferior facets 10a and 10b, lamina 5a and 5b, posterior arch 16 and spinous process 18 of superior vertebra 2 of FIG. 1A may be resected for purposes of implantation of certain of the dynamic stabilization systems of the present invention. In other applications, where possible, the natural facet joints, lamina and/or spinous processes are spared and left intact for implantation of other dynamic stabilization systems of the present invention.

It should also be understood that the term "system", when referring to a system of the present invention, most typically refers to a set of components which includes multiple bone stabilization components such as a superior, cephalad or rostral (towards the head) component configured for implantation into a superior vertebra of a vertebral motion segment and an inferior or caudal (towards the feet) component configured for implantation into an inferior vertebra of a vertebral motion segment. A pair of such component sets may include one set of components configured for implantation into and stabilization of the left side of a vertebral segment and another set configured for the implantation into and stabilization of the right side of a vertebral segment. Where multiple bone segments such as spinal segments or units are being treated, the term "system" may refer to two or more pairs of component sets, i.e., two or more left sets and/or two or more right sets of components. Such a multilevel system involves stacking of component sets in which each set includes a superior component, an inferior component, and one or more medial components therebetween.

The superior and inferior components (and any medial components therebetween), when operatively implanted, may be engaged or interface with each other in a manner that enables the treated spinal motion segment to mimic the function and movement of a healthy segment, or may simply fuse the segments such as to eliminate pain and/or promote or enhance healing. The interconnecting or interface means include one or more structures or members that enables, limits and/or otherwise selectively controls spinal or other body motion. The structures may perform such functions by exerting various forces on the system components, and thus on the target vertebrae. The manner of coupling, interfacing, engagement or interconnection between the subject system components may involve compression, distraction, rotation or torsion, or a combination thereof. In certain embodiments, the extent or degree of these forces or motions between the components may be intraoperatively selected and/or adjusted to address the condition being treated, to accommodate the particular spinal anatomy into which the system is implanted, and to achieve the desired therapeutic result.

In certain embodiments, the multiple components, such as superior and inferior spinal components, are mechanically coupled to each other by one or more interconnecting or interfacing means. In other embodiments, components interface, in a manner that constrains their relative movement and enables the treated segment to mimic the function or partial function and/or movement or partial movement of a healthy segment. Typically, spinal interconnecting means is a dorsally positioned component, i.e., positioned posteriorly of the superior and inferior components, or may be a laterally positioned component, i.e., positioned to the outer side of the posterior and inferior components. The structures may include one or more struts and/or joints that provide for stabilized spinal motion. The various system embodiments may further include a band, interchangeably referred to as a ligament, which provides a tensioned relationship between the superior and inferior components and helps to maintain the proper relationship between the components.

Reference will now be made in detail to the present embodiments of the invention, examples of which are illustrated in the accompanying drawings. Wherever possible, the same reference numbers will be used throughout the drawings to refer to the same or like parts. In addition, each of the inventive embodiments described herein may be employed in a percutaneous procedure, a mini-open procedure or an open procedure. Utilization of minimally invasive techniques can shorten the procedure's time and speed recovery by the patient. The application of these inventions in a minimally invasive manner is not a requirement.

Figure 2A:
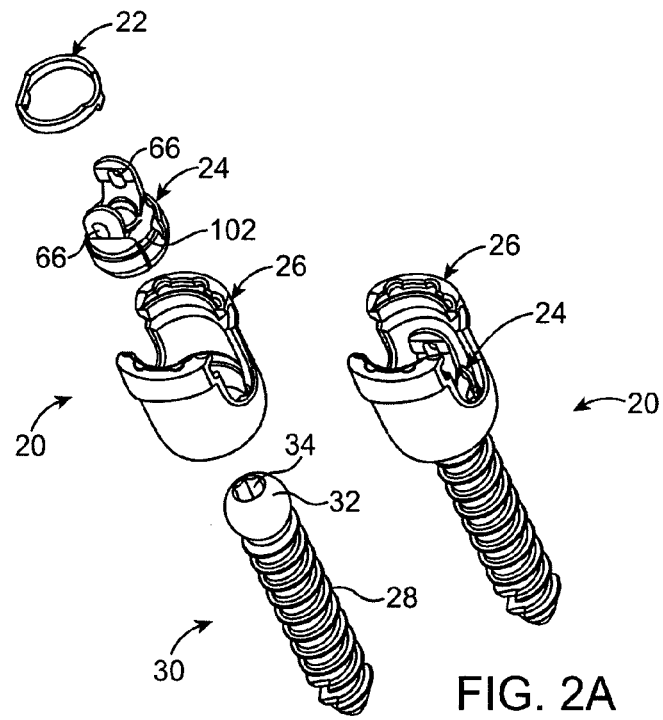
FIG. 2A illustrates a perspective exploded and perspective view of a screw system which may be employed in an embodiment of the present invention.

FIG. 2A illustrates a perspective exploded and perspective view of a screw system which may be employed in an embodiment of the present invention. In this figure, a screw system 20 is shown having a screw 30 with threads 28. The threads 28 are appropriate for entering the bone of a patient. At a proximal end of screw 30 is a ball end 32. While a ball end 32 is shown, various other shapes may also be employed. A hex socket 34 that is interconnected with a guidewire lumen (not shown) extends thru the general axial center of screw 30, and also can extend through the retaining ring 22, coupler 24 and seat 26. The system is suitable for being installed in a patient for treating at least one or more of the following: degenerative disc disease, spinal stenosis, spondylolisthesis, spinal deformities, fractures, pseudarthrosis, tumors, failed previous fusions, other vertebral segment trauma or diseases.

The ball end 32 of screw 30 is fitted into the bottom of the coupler 24, which has a spherical interior shape, as will be described in greater detail below. If end 32 has a different shape, the shape of the interior of the bottom of the coupler 24 may be similarly complimentary. No matter the shape, when the ball end is fitted into the bottom end of end of the coupler 24, the coupler 24 may be fitted into the "bucket-shaped" seat 26. Retaining ring 22 ensures that coupler 24 does not escape from the interior of seat 26, and is described in greater detail below.

Figure 2B:
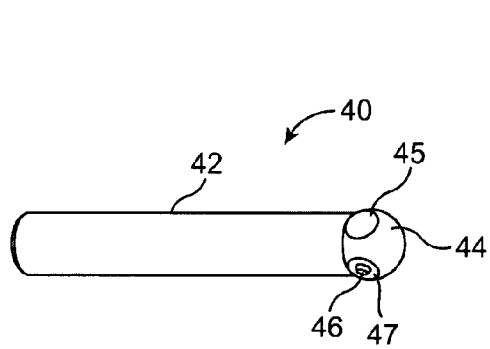
FIG. 2B illustrates a perspective view of a pivoting rod which may be employed in an embodiment of the present invention.

FIG. 2B illustrates a perspective view of a pivoting rod 40 which is employed in an embodiment of the present invention. The pivoting rod 40 in FIG. 2B is shown to be straight, however, the invention is not so limited and a curved pivoting rod that conforms to the natural curve of the spine may be employed. The pivoting rod 40 has a shaft 42, a ball end 44, and two pins 46 (one of which is not shown in FIG. 2B) for insertion into the coupler 24. The shaft 42 may vary in length, or may be adjustable by the physician, either by a telescoping mechanism or by being cut to measure. The end of the shaft 42 opposite that of ball end 44 may be straight, as shown, or may itself incorporate a ball end (not shown) or other type of end to enable trapping and capture in a seat of a pedicle screw system mounted to another spinal segment. The ball end 44 need not actually be a ball, and may be a square or rectangular solid, or other such shape, so long as the shape allows rotation of the pivoting rod. In general, the rod 40 and coupler 24 include mating features adapted to connect together.

As shown in FIG. 2B, sides 47 of the ball end, perpendicular to the pins 46, are flattened. The flat sides 47 that are substantially perpendicular to the pins 46 also assist in confining the range of motion of the rod substantially within a single plane. Furthermore, the flattened sides 47 surrounding the pins 46 provide for a greater surface area that is in contact with the coupler 24 and thereby create an advantageous snug-fit engagement with the coupler. Because of the flattened sides 47, when the rod 40 is inserted and the pins 46 are connected into the coupler 24, the greater surface area of contact of the flattened sides 47 with the coupler provides for a snug-fit engagement with the coupler that would otherwise be the case with a rounded rod end. As a result, the rod advantageously does not pivot on its own in a direction away from the insertion angle or other angle at which the rod is positioned subsequent to insertion into the coupler. This feature facilitates insertion for the surgeon.

In another variation, additional flat portions 45 are formed on the ball end 44 of the rod 40 as shown in FIG. 2B. The flat portions 45 are substantially perpendicular to the flattened sides 47 on the ball end 44. The pins 46 are substantially parallel to the flat portions 45. When the rod is inserted into the seat and pivoted into a generally horizontal position, the flat portions 45 face upwardly and downwardly and as a result provide a lower profile for the rod within the seat. Furthermore, the flat portions 45 provide a flat contact surface for the set screw on the upper surface of the rod and a flat contact surface for the coupler on the bottom surface of the rod. The rod is not limited to having two flat portions 45 and/or two flattened sides 47 and any number and combination of flat portions 45 and sides 47 are within the scope of the present invention.

Figure 2C:
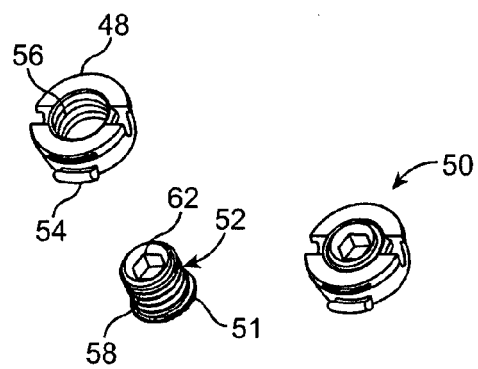
FIG. 2C illustrates a perspective exploded and perspective view of a cap and set screw system which may be employed in an embodiment of the present invention.

FIG. 2C illustrates a perspective exploded and perspective view of a closure mechanism 50. The closure mechanism is shown as a cap and set screw system 50 which may be employed in an embodiment of the present invention. It should be noted that the closure mechanism is not limited to a cap and set screw combination as shown and described herein and various other closure mechanisms evident to a person having ordinary skill in the art are within the scope of the invention. Some examples of closure mechanisms include but are not limited to a threaded closure mechanism having external threads that engage with a threaded internal portion of the seat, a sliding closure mechanism, a compression fit closure mechanism, and a snap fit closure mechanism. The closure mechanism 50, when fully installed in the seat 26, secures the rod 40 against movement. In one variation, the system 50 includes a cap 48 and a set screw 52. The cap 48 includes a set screw receiving portion. The cap and set screw are configured to close the top opening of the seat 26. The external shape of the cap 48 is substantially cylindrical. The cap 48 includes a top surface and a bottom surface interconnected by an outer surface and an inner surface. The cap 48 includes external flanges or features 54, discussed in more detail below, and internal screw threads 56.

The set screw 52 includes external screw threads 58 and a socket 62 for a driving tool, the socket 62 being substantially coaxial with the screw threads 58. The set screw 52 also includes a flange 51 at the bottom end of the set screw 52. The flange 51 is configured to extend outwardly from the circumference of the set screw to serve as a stop and to prevent the set screw 52 from being backed-out as the set screw is retracted upwardly with respect to the cap 48.

Various aspects and alternative embodiments of this basic system are described below. In this regard, it is noted that the above system of FIGS. 2A-2C would typically be employed in the following fashion: a first pedicle screw assembly would be installed in a patient, this first pedicle screw assembly having a hinge assembly that attaches to a proximal end of the pivoting rod. A second pedicle screw assembly would also be installed in a patient, this second pedicle screw assembly having a receiving cradle that accepts the distal end of the pivoting rod. Except for the hinge assembly and the receiving cradle, other parts of the screw assemblies may be the same and/or interchangeable. Each pedicle screw assembly also includes a set screw and cap assembly as described above and below. Further, the pivoting rod may include a dynamic element at some point along its length if desired, as described, e.g., in U.S. patent application Ser. No. 11/427,738, filed Jun. 29, 2006, U.S. patent application Ser. No. 10/970,366 filed Oct. 20, 2004, U.S. patent application Ser. No. 11/006,495 filed Dec. 6, 2004, U.S. patent application Ser. No. 11/033, 452 filed Jan. 10, 2005, and U.S. patent application Ser. No. 11/436,407 filed on May 17, 2006, all of which are incorporated by reference herein in their entirety for all purposes.

Figure 2D:
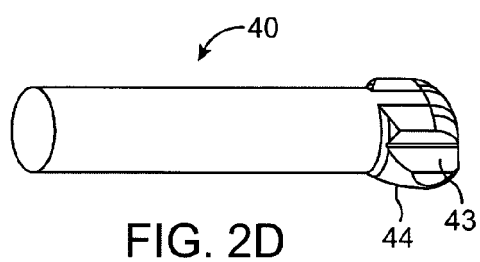
FIG. 2D illustrates a perspective view of a pivoting rod which may be employed in an embodiment of the present invention.
Figure 2E:
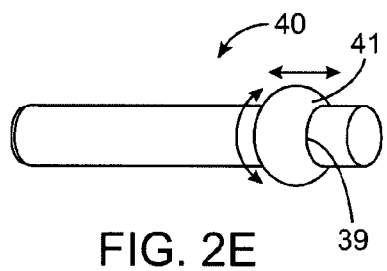
FIG. 2E illustrates a perspective view of a pivoting rod which may be employed in an embodiment of the present invention.

First, referring back to FIG. 2B, the pivoting rod 40 is shown with integral pins 46 that are configured to snap-fit with the coupler 24 to secure the rod 40 in place and permit rotation of the rod. In one variation, the pins 46 are chamfered to ease the insertion of the pivoting rod by the clinician into the coupler and also ease removal of the pivoting rod from the coupler, if desired. Pins are not the only means of attachment of the rod 42 to the coupler 24 and other variations and means are within the scope of the invention. For example, as shown in FIG. 2D, the ball end 44 of the rod can include cutout portions 43 that result in the ball end not having a completely spherical shape but permits attachment to and rotation relative to the coupler 24. Another example is shown in FIG. 2E. In FIG. 2E, a rod 40 is provided with a ball portion 41 having a bore 39 passing through it. The rod 40 of FIG. 2E is positioned inside the bore 39 of the ball portion 41 such that the ball portion 41 is allowed to rotate and slide relative to the rod as indicated by the arrows in FIG. 2E. This embodiment advantageously provides yet another degree of freedom of motion and facilitates installation by the surgeon. Furthermore, the embodiment of FIG. 2E advantageously permits the bone screw to be locked into position independently of rod and in another variation it permits the rod to be locked into position independently of the bone screw. More details of the independent lock down capability of this embodiment will be described in greater detail hereinbelow.

An alternative way in which the pivoting rod 40 may be attached to the coupler that employs pins is shown in FIG. 3 and FIG. 3A. In particular, a set of two pins 64 may be employed which mate with a corresponding set of holes 66 in the coupler. As shown in FIG. 3A, the pin 64 may be spring-loaded with springs 68. This spring-biased hinge pin allows pivoting of the rod and also allows the pin to move radially inward during insertion, and then "pop" out when in place. The pin may then be retracted for removal. In an alternative embodiment, the pin may be permanently locked in place by injecting cement or glue or another such material into the travel volume of the pin.

Another variation for the rod-end system is shown in FIG. 4 and the enlarged views of FIG. 4A-4C in which the pivoting rod 40 is attached to the coupler via pins 72. In this case, pins 72 may again be spring-biased but may be movable via action of a set screw 76. In particular, and as shown in FIGS. 4A and 4B, pins 72 are biased by springs 74 in a retracted state; i.e., they are not extended so as to engage or mate with holes in the coupler. Instead, a portion of the pins 72 extends into a threaded hole 70 within a proximal end of pivoting rod 40, i.e., ball end 44. When a set screw 76, with conical distal surface 82, is advanced into the threaded hole 70, the distal surface 82 impinges on pins 72 and drives the same outward, such that they may engagedly mate with the holes in the coupler. The set screw 76 may have a slot 78 and/or other tool engagement means (not shown) in its proximal (top) surface to allow for such driving. In this way, the extendable/retractable hinge pins extend after insertion to pivotally lock the pins in place.

In an alternative embodiment to FIGS. 4 and 4A-4C, the extension and retraction may be accomplished with hydraulics or pneumatics, rather than springs and set screws. To this end, a fluid injection port may be provided which is integral, or not, to the pivoting rod. In a further alternative embodiment, the pins may be permanently locked in place, if desired by the physician, by injecting cement or glue into the pin travel volume. Although the rod has been described as being configured to connect to the coupler the invention is not so limited and in alternative variations, the rod is configured to connect to the seat or retainer.

Figure 5A:
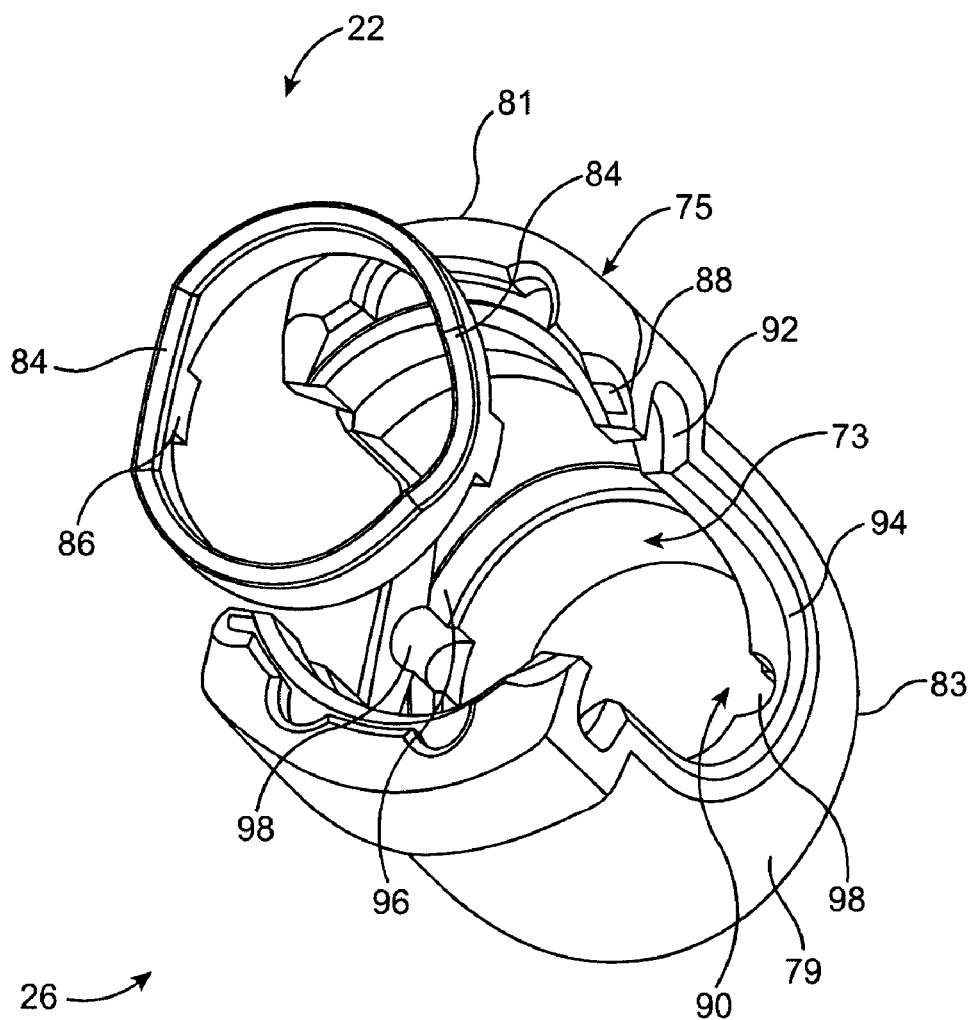
FIG. 5A is a perspective detailed view of a seat and retaining ring according to an embodiment of the present invention.

Various aspects of the seat, coupler, and retaining ring are now discussed. Referring to FIG. 5A, a seat 26 and retaining ring 22 are shown in an exploded view. Retaining ring 22 is shown with two projections 86, also known as keys, which engage features on the seat 26, to hold the coupler in place (the coupler is not shown in the figure for clarity). Ring rod channel bevels 84 are shown on opposite ends of a diameter of the ring, adjacent the projections 86, although in alternative embodiments they need not be adjacent. Ring rod channel bevels 84 are depressed areas along an upper surface of the circumference of the ring 22, and assist in receiving the pivoting rod (also not shown for clarity). Another variation of the retaining ring 22 is shown in FIG. 8B. The retaining ring 22 of FIG. 8B includes a split such that the retaining ring 22 is approximately C-shaped. The split retaining ring 22 snaps into place inside the seat 26 to secure the assembly.

Figure 5B:
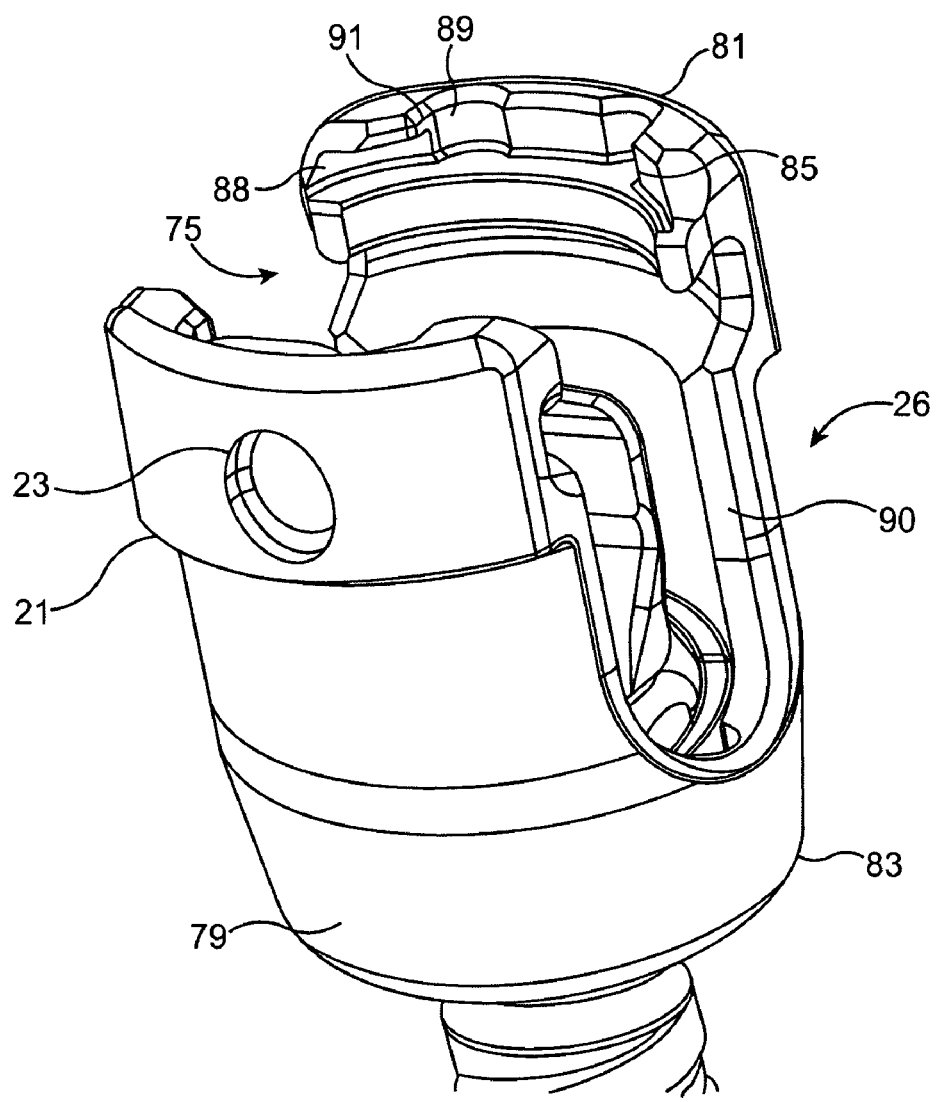
FIG. 5B is a perspective view of a seat, coupler, retaining ring and screw according to an embodiment of the present invention.

Still referencing FIG. 5A and with particular reference to FIG. 5B, the seat 26 includes an inner surface and an outer surface and a first end 81 and a second end 83. At least one sidewall 79 extends between the first end 81 and the second end 83 forming a top opening at the first end 81 and at least one "U"-shaped void or rod channel 90 into which the pivoting rod may pivot when installed. Two rod channels 90 or voids and shown in FIG. 5A in which voids 90 are defined in part by seat rod channel bevels 94. A void or keyway 98 is provided near the base of the seat to engage each projection 86 to orient the ring in a press-fit fashion with respect to the coupler and seat. In FIG. 5A, the keyways 98 are adjacent the rod channel bevels 84 and 94 because the keys 86 are adjacent the same; however, the keys and keyways need not be along the same diameter as the bevels. The ring and seat rod channel bevels may generally match each other in shape, pitch, angle, slope, etc., and assist in orienting the rod pivot arc as well as orienting the rod channel to receive the rod on the cradle or receiving assembly.

The seat 26 includes a closure mechanism receiving portion or a cap receiving portion 75 configured to receive a cap at the first end 81 and a coupler receiving portion 73 configured to receive a coupler. The coupler receiving portion 73 includes a tapered ramp that corresponds to a tapered ramp on the coupler. The cap receiving portion 75 includes a locking lug groove 88 that is provided near the top of the seat 26 to slidingly receive a corresponding locking lug or projection of the cap, described below. Cap rotation of, for example 90 degrees, secures the cap in place. The locking lug groove 88 may further include an anti-rotation mechanism, such as a mechanical stop. In this way, the locking lugs may be fixed in the amount of rotation needed to secure them in place. A wing groove 92 is also provided on the seat 26, to slidingly receive and engage a corresponding wing lug or projection on the cap, as described below. The wing groove 92 may also be provided with a mechanical stop that prevents further rotation of the wing within the wing groove similar to the locking lug groove. On the outside surface of the seat 26, a flange 21 and two recesses 23 in opposed locations are formed as shown in FIGS. 5A and 5B. The flange has an upper surface, lower surface and an outer surface.

Figures 6A, 6B:
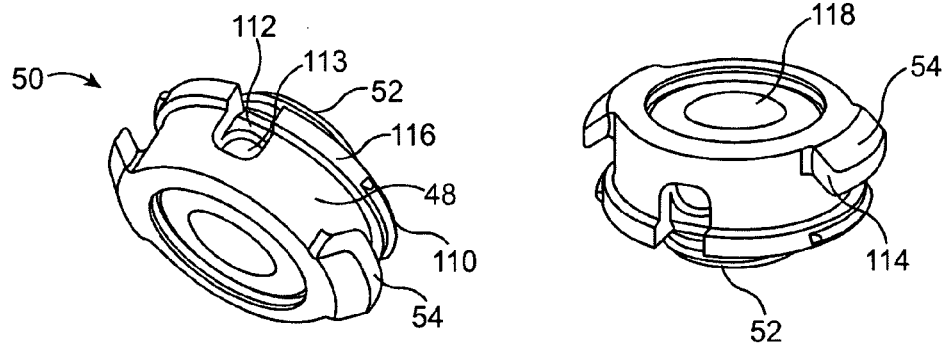
FIGS. 6A and 6B illustrate bottom perspective and top perspective views of a cap and set screw system according to an embodiment of the invention.

FIGS. 6A-6B show bottom and top perspective views, respectively, of the cap system 50 having cap 48 and set screw 52. The cap 48 incorporates at least one groove 112 and recess 113 for engagement with an inserter or driving tool to accomplish the partial rotation needed to lock the cap 48 into the seat 26. The inserter or driving tool may grip the cap for rotation: the recess provides room for "tangs" of the inserter tool, and the groove allows the "tangs" to clear the inner surfaces of the seat. A flange 116 may be provided which is an annular projection at the top surface. The flange 116 acts as a mechanical stop, to limit the amount of insertion of the cap into the seat. The outer surface of the cap includes at least one seat-engagement feature for engagement with the cap-receiving portion of the seat.

One seat-engagement feature on the cap is at least one locking lug 110 that is provided in at least one location around the circumference of the cap 48 and extending from the outer surface of the cap. As shown in FIGS. 6A and 6B, two locking lugs 110 are provided on or are integral with the flange 116 opposite from one another. The locking lugs 110 are sized for insertion into the rod channel 90. Also, the locking lugs 110 are configured to be rotatably inserted into the locking lug groove 88 in the seat 26. Typically, the locking lugs 110 are first inserted into the rod channel 90 and then rotated into position inside the locking lug groove 88.

Another seat-engagement feature on the cap is at least one wing 54 that is provided in at least one location around the circumference of the cap 48 extending outwardly from the outer surface of the cap. As shown in FIGS. 6A and 6B, two wings 54 are provided in opposed locations around the circumference of the cap 48. The two wings 54 are aligned with the two locking lugs 110 wherein the wings 54 are located below locking lugs 110. The wings are sized for insertion into the rod channel 90. Also, the wings are configured to be rotatably inserted into the wing groove 92. Generally, the cap 48 is placed into the seat 26 with the two wings 54 and the two locking lugs 110 in alignment with the rod channel 90 such that the cap 48 drops into the seat until the flange 116 abuts a surface of the locking lug groove 88. After the cap is seated, it is capable of being turned. Turning of the cap 48 rotates the wings 54 and the locking lugs 110 into the wing grooves 92 and locking lug grooves 88, respectively. To effect the rotation, a tool is used to engage the groove 112 and/or recess 113 of the cap to turn the cap 48 while it is inside the seat.

In one variation, as shown in the perspective close-up view of the seat 26 in FIG. 5B, the cap (not shown) is turned until rotation is stopped by a wall 85 located in the locking lug groove 88 against which the locking lugs 110 abut. A second locking wall (not shown) may also formed in the opposite locking lug groove generally diagonally from wall 85. The degree of rotation is preferably approximately 90 degrees but the invention is not so limited and any degree of rotation is within the scope of the invention. The wall serves as an anti-rotation mechanism that prevents the cap from turning past a locked position. Other anti-rotation mechanisms may also be employed.

In one variation, after the cap 48 is seated and rotated such that the wings 54 and locking lugs 110 are in the wing grooves 92 and locking lug grooves 88, respectively, a set screw 52 located inside the cap 48 is tightened. As the set screw 52 is tightened, the cap 48 rises relative to the seat 26, that is, the cap will move upwardly relative to the seat. This rise is arrested by the wings 54, also known as wing lugs, contacting the upper surface of the wing groove 92. In an alternative variation, the locking lugs alone or in conjunction with the wings are employed to arrest the rise of the cap as the set screw is advanced and a force, resulting from the set screw being biased against the seat, is applied to the rod below the set screw.

Furthermore, in one variation, counter-rotation of the cap 48 is prevented as the set screw is advanced and the locking lugs 110 rise relative to the seat 26 into a recess 89 or window formed inside the locking lug groove 88 as shown in FIG. 5B. The recess or window 89 includes a stop 91 against which the locking lugs 110 abut to prevent counter-rotation. After the cap 48 has moved upwardly upon set screw advancement such that the locking lugs 110 have substantially entered the recess or window 89, the locking lugs 110 are substantially moved out of the locking lug groove 88 and they cannot be moved back into the groove 88, and thus the cap cannot be removed, until the set screw is "backed off" and the cap drops or is "lowered" such that the locking lugs 110 reside again in the groove 88. It should be noted that a corresponding recess 89 and a corresponding wall 91 is formed in the other side of the cap receiving portion of the seat.

The wing 54 has a reverse angle surface 114 to inhibit spreading of the seat. The wing or wing lug groove 92 defined by the interior of seat 26 slidingly receives the wing 54 or wing lug of the cap 48, and the cap is locked into the seat when the cap is rotated, for example, by 90 degrees. The reverse angle surface 114 keeps the seat 26 from splaying as the set screw 52 is rotated. In particular, as the set screw 52 rotation forces the cap upwards, the reverse angle surface 114 keeps the walls of the seat 26 from spreading outward. Otherwise, the forces of the cap upward movement would tend to spread the seat.

In an alternative embodiment, the wings may snap into recesses of the wing lug groove 92 when an appropriate or predetermined degree of rotation has been achieved. Appropriate spring-loading may be employed to achieve this snapping feature.

As shown in FIGS. 6A and 6B, in one variation, the bottom surface of the set screw 52 includes a dome 118 that protrudes from the bottom surface of the set screw 52. As the set screw 52 is advanced, the feature 118 contacts the rod 40 and creates a single point, line or smaller surface area of contact than would otherwise be the case between the cap system 50 and the rod 40. This restrains less of the rod, allows some flexion and thus reduces the stiffness of the total device between the screws, leading to a better stress distribution through the construct, a lower stress concentration and enhanced fatigue performance. Examples of other features in the bottom surface of the set screw include but are not limited to any one or more of the following used alone or in combination: a dome, nipple, aperture, raised surface, and a dome with an aperture.

Figure 7:
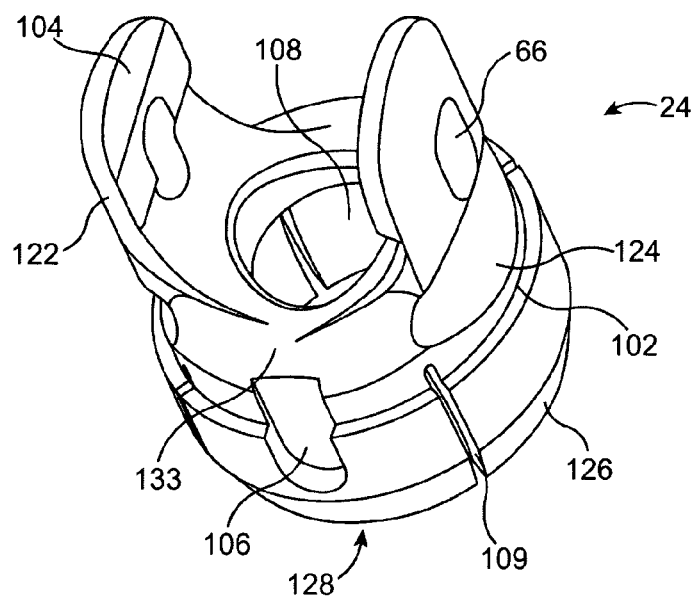
FIG. 7 illustrates a perspective view of a coupler system according to an embodiment of the invention.

FIG. 7 shows additional details of the coupler 24. The coupler 24 generally has a bone screw receiving portion 128 and a rod receiving portion 122. The rod receiving portion is shown in one variation as two upstanding forks 122 each of which has a receiving hole 66 for receiving the rod pin. The upstanding forks 122 may have a tapered end, a closed end and/or an open end. FIG. 7 shows a beveled region 124 radially exterior of each fork that lessens the amount of material in each fork, allowing greater amounts of flex. The coupler access bore hole 108 provides access to the engagement means of the screw such as a hex socket. The inner surfaces of the rod receiving portion of the coupler and the screw head receiving portion are provided with grit-blasting to increase the surface roughness and resultant friction coefficient between the coupler and/or the rod.

Still referencing FIG. 7, a lip 102 is provided to mate with the retaining ring 22. An approximately spherical bore 128 or screw head receiving portion is provided in the interior of the bottom of the coupler 24 that "snap-fits" over the head 32 of the screw 30 to allow a limited amount of rotation, for example 60 degrees of polyaxial rotation. The exterior surface of the coupler, exterior of the spherical bore 128, may be a generally tapered ramp 126. Slits 109 may further be provided to allow circumferential compression around the screw head.

With the cap in the cap-receiving portion of the seat and as the set screw is advanced within the cap, the screw contacts the rod and the cap rises relative to the seat until the wing lugs contact the upper surface of the wing lug groove and the cap is thereby biased into a locked configuration by the seat. Further advancement of the set screw exerts additional force onto the rod and it is transferred to the coupler and drives the coupler downward. As the set screw drives the coupler downward, e.g., through a force transmitted through the rod, the coupler is pushed downward, further into the seat. The tapered ramp of the coupler engages the corresponding tapered ramp in the seat. The coupler is radially compressed (which is possible because of the slits 109), thus gripping the screw head securely and simultaneously locking the bone screw and the rod into the desired position. In one variation, the lockdown of the bone screw does not occur simultaneously with the lockdown of the rod. For example, if the rod embodiment of FIG. 2E is employed, advancement of the set screw contacts the ball portion 41 that slides and rotates with respect to the rod 40. The contact with the set screw transmits force directly to the coupler to effect the lockdown of the bone screw relative to the seat without locking down the rod relative to the seat, thereby, allowing the rod to slide and rotate with respect to the ball portion 41. Further advancement of the set screw compresses the ball portion 41 locking the rod into position relative to the ball portion 41 after the bone screw has been locked. In an alternative variation, the advancement of the set screw contacts the ball portion 41 and compresses the ball portion 41 to effect lockdown of the rod with respect to the seat without locking down the bone screw relative to the seat. Further advancement of the set screw transmits force to the coupler to effect lockdown of the bone screw relative to the seat after the rod has been locked first. This independent lockdown mechanism permits the selective lockdown of the rod relative to the seat and bone screw relative to the seat. Prior to the set screw being tightened, the bone screw and rod each were allowed movement relative to the seat. After the set screw is tightened, movement of both the bone screw and rod is generally eliminated. Hence, the cap set screw system in combination with the seat and coupler provide a lockdown mechanism just described that operates between a locked configuration in which the rod and the bone screw are locked into position and an unlocked configuration in which the rod and the bone screw each have a range of motion relative the seat. It is noted that with the cap positioned in the seat, the rod is not in vertical alignment with the seat, but instead, at least a portion of the rod extends through the rod channel 90. However, the rod still retains a range of motion while disposed in the rod channel and in the unlocked configuration. It should be noted that in one variation of the present invention, the system permits some degree of motion of the rod and bone screw even when the system is in the locked configuration. Also, there may even be additional structural elements employed to permit some degree of motion while in the locked configuration. Some examples of such elements include, a reduced point of contact with the set screw as described herein and shock absorption elements deployed between the coupler and the seat for example. Hence, the term "locked" is used to describe the restriction of motion of the rod and/or screw relative to the unlocked configuration. Also, the term "locked" is used with respect to the cap to describe the cap being seated inside the seat whether or not the set screw is advanced to the locked configuration to set the position of the rod and/or screw.

A recess or keyway 106 is provided in which a driving tool may be disposed to receive the keys or projections 86 on the retaining ring 22. Especially for use on the hinged assembly version, a "lead-in" ramp 104 may be employed as a chamfered edge, providing a mechanical advantage to spread the coupler forks. To this end, the forks may be configured to flex and also be resiliently biased. All of these features allow the hinge pins to more conveniently slide in and snap securely into the receiving holes 66.

Especially for use on the receiving cradle assembly embodiment, the coupler may be generally the same and may further include a smooth surface 133 which incorporates a radiused edge which increases the contacting surface area and reduces high stress concentrations. In this way, the rod may be even more tightly received between the forks reducing the stress concentration on the rod and coupler.

Figure 8A:
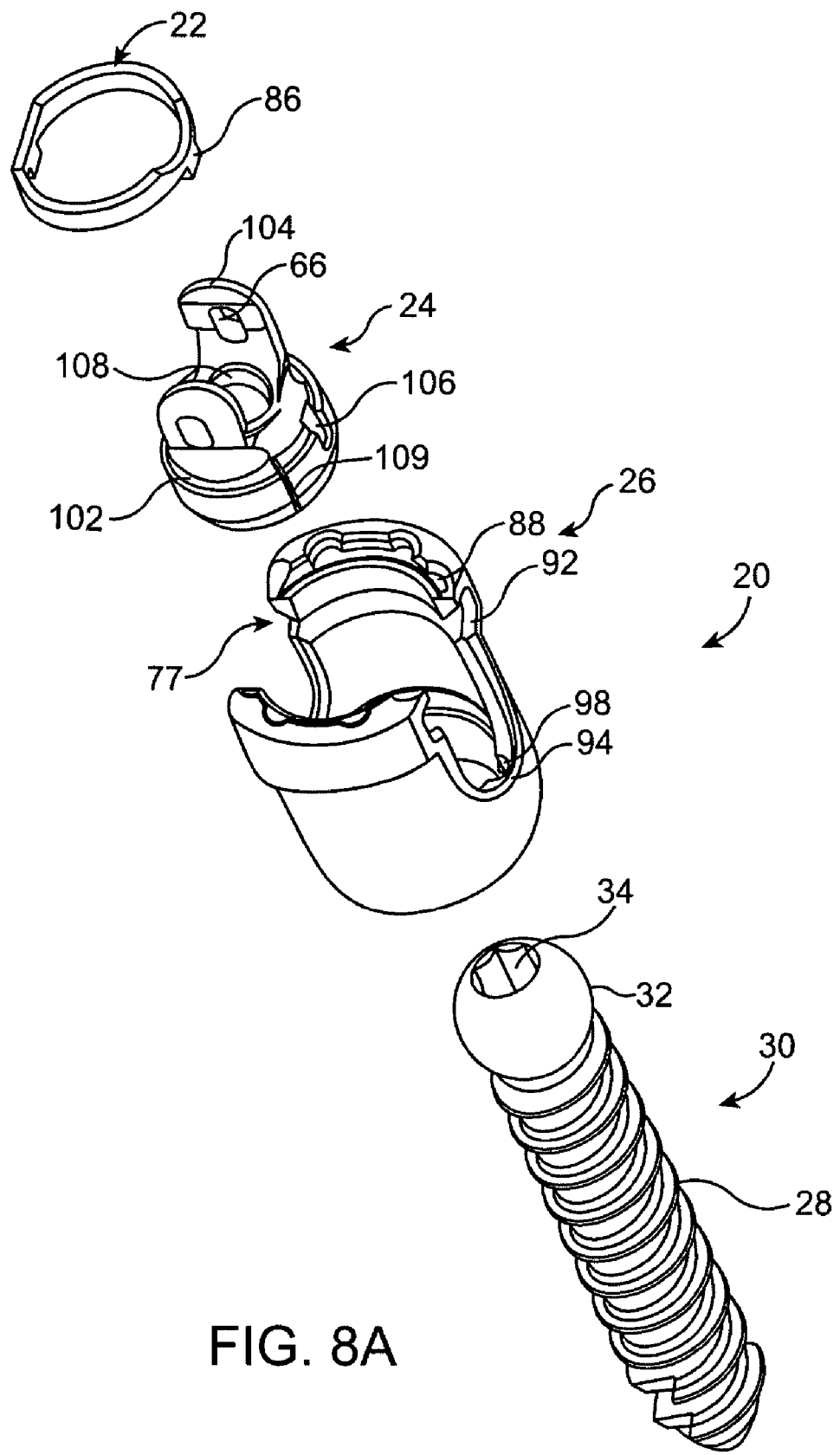
FIG. 8A illustrates a perspective exploded view of a screw system according to an embodiment of the present invention.
Figure 8B:
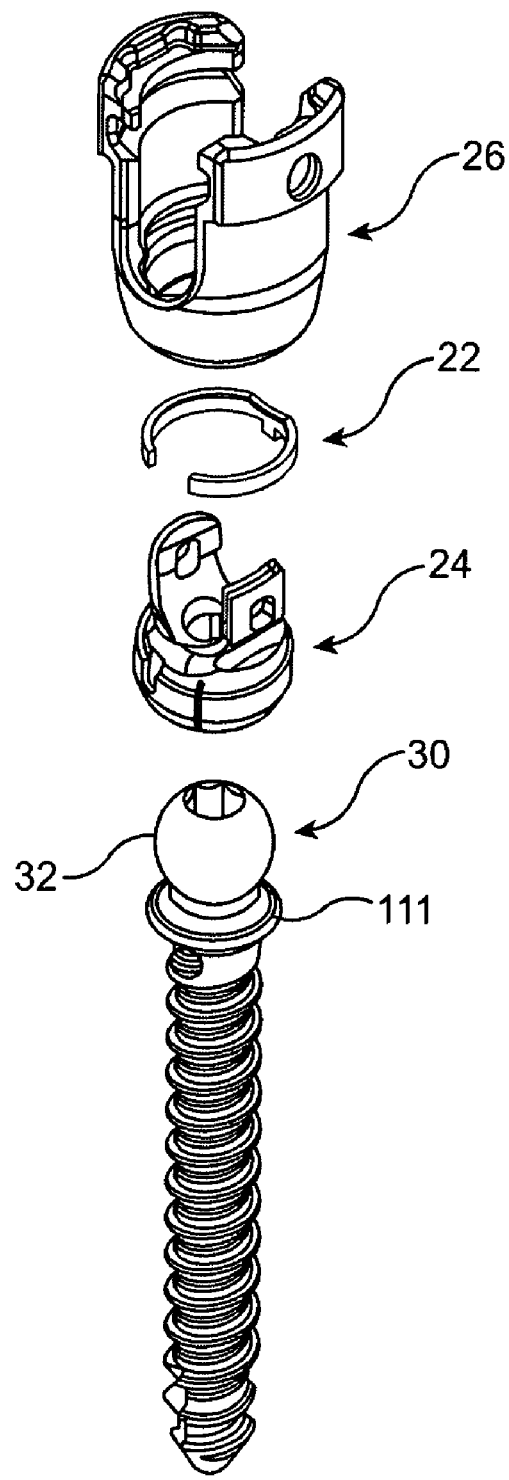
FIG. 8B illustrates a perspective exploded view of a screw system according to an embodiment of the present invention.

FIG. 8A is a more expanded view of FIG. 2A. The basic four set of components, ring, coupler, seat, and screw, may be the same or similar for both the hinged assembly and the receiving cradle. The seat snaps onto the screw, the coupler is placed into the seat, and the ring is press-fitted into the seat to retain the coupler. To this end, the seat 26 may have an internal tapered bore to hold the coupler and screw in a snug configuration.

Figure 8C:
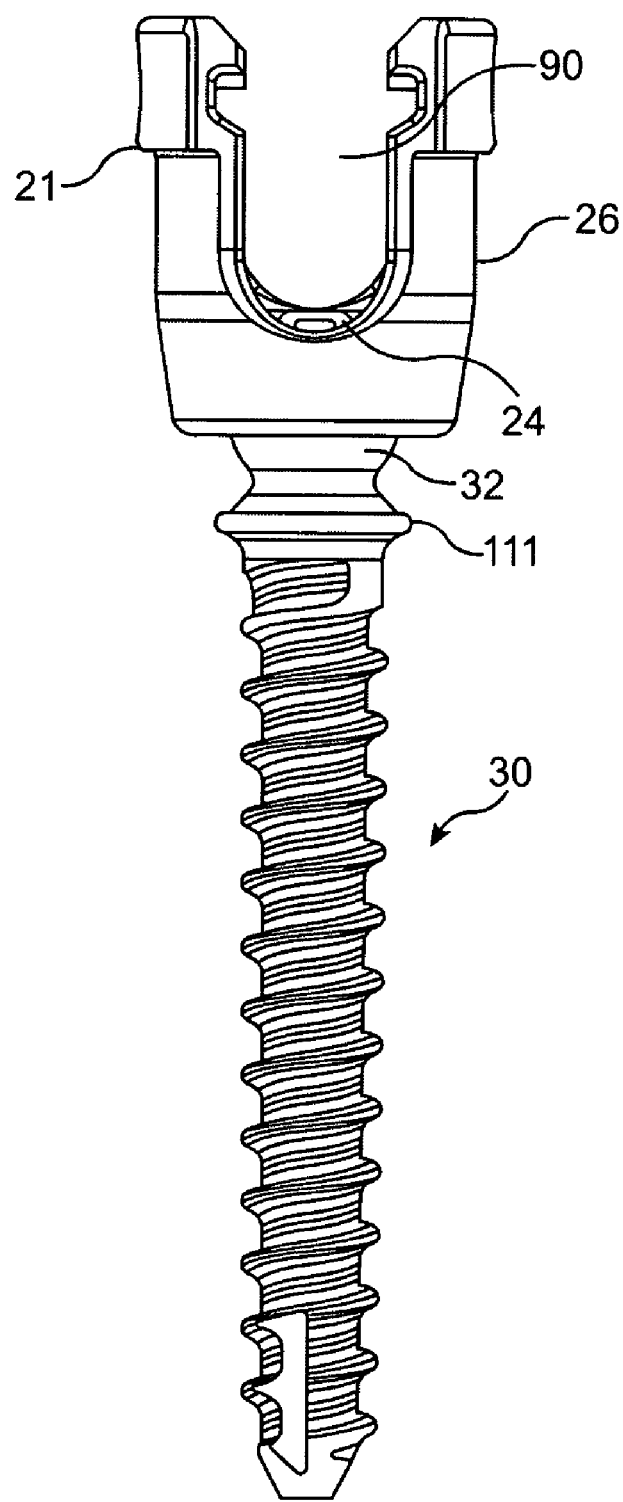
FIG. 8C illustrates a side elevational view of a screw system according to an embodiment of the present invention.

FIG. 8B is a perspective view of another variation of the present invention showing the screw 30, seat 26, coupler 24 and retaining ring 22 in an exploded view and FIG. 8C is a side-elevational view of the system wherein like elements are referenced with like numerals. In the variation shown in FIGS. 8B and 8C, the screw includes a flange 111 located below the screw head 32. The flange 111 extends outwardly from and around the screw; however, the invention is not so limited and the flange 111 may be noncontinuous forming two or more flange pieces around the circumference of the screw for example. The flange 111 is configured to serve as a stop and prevent the screw from being inserted into the bone beyond the flange. Hence, the flange 111 is sufficiently broad that it does not dig into the bone as the screw is attempted to be advanced beyond the flange-to-bone contact. Preferably, the flange surrounds the circumference of the screw at a distance below the screw head that permits maximum angular and polyaxial adjustment and rotation of the seat. The flange 111 may be formed or located closer to the screw head to constrain the degree of freedom of the polyaxial adjustment and rotation of the seat if it is so desired. Furthermore, the flange advantageously provides a tactile signal to the clinician when the flange 111 abuts the bone when inserting the screw into the bone. Without the tactile signal provided by the screw flange, the clinician must verify advancement of the screw under fluoroscopy to avoid the screw head being completely driven to the surface of the bone which would impede the ability of the polyaxial seat to rotate and angulate freely. Because the flanged screw facilitates screw insertion, it is particularly advantageous in minimally invasive procedures.

As mentioned above, the retaining ring 22 of FIG. 8B includes a split such that the retaining ring 22 is approximately C-shaped. To assemble the screw system shown in FIG. 8B, the bone screw head 32 is inserted into the coupler 24 and the split retaining ring 22 is inserted into the seat 26.

The screw and coupler assembly is passed through the top of the seat 26 and attached together to complete assembly of the screw system.

Figure 9D:
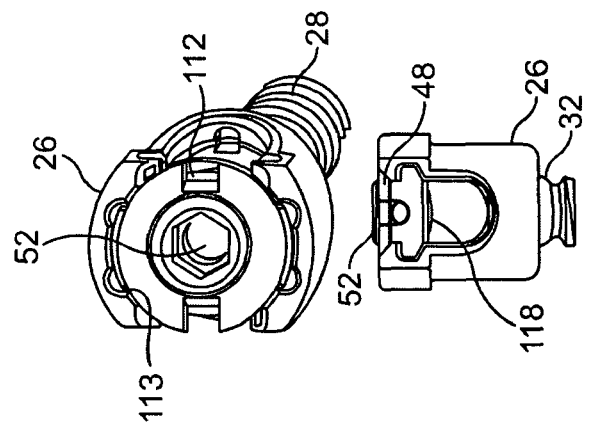
FIGS. 9B-9D illustrate the combination system of FIG. 9A in unlocked, partially locked, and fully locked configurations.
Figure 9C:
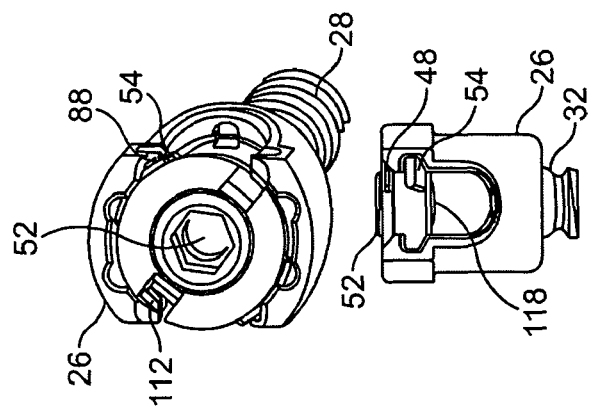
Figure 9B:
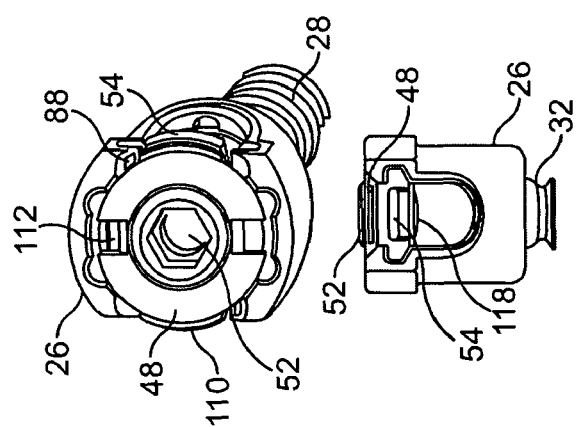
Figure 9A:
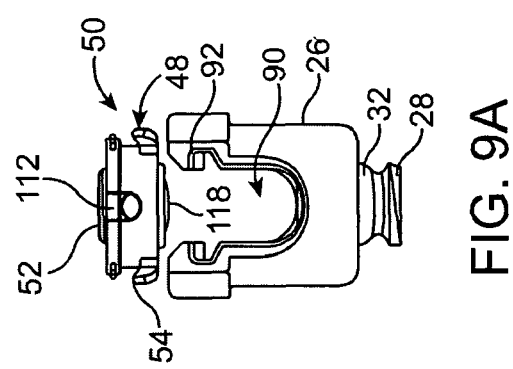
FIG. 9A illustrates a side exploded view of a screw/seat/cap and set screw combination.

Various methods of use are now described with respect to FIGS. 9A-9D. In use, the set screw 52 is partially advanced into the cap 48 and the same is situated above the seat 26 as shown in FIG. 9A. In FIG. 9A, for clarity, the locking lugs and the wings of cap 48 are half in-the-page and half out-of-the-page. In the same way, one rod channel is below the page and the other is above the page.

As shown in both views in FIG. 9B, the cap is rotated 90 degrees with respect to the orientation of FIG. 9A, and the same is placed into the seat. The locking lugs and wings are shown in the general area of the rod channel 90. Using the cap inserter groove, the cap is then rotated to lock the same into position. FIG. 9B shows an approximately 45 degrees turn counter-clockwise. In this configuration, the cap is partially locked onto the seat. In FIG. 9D, the cap has been rotated 90 degrees with respect to the orientation of FIG. 9B, and the cap is now locked onto the seat. A mechanical stop 91 may be employed to prevent further rotation.

Figure 10A:
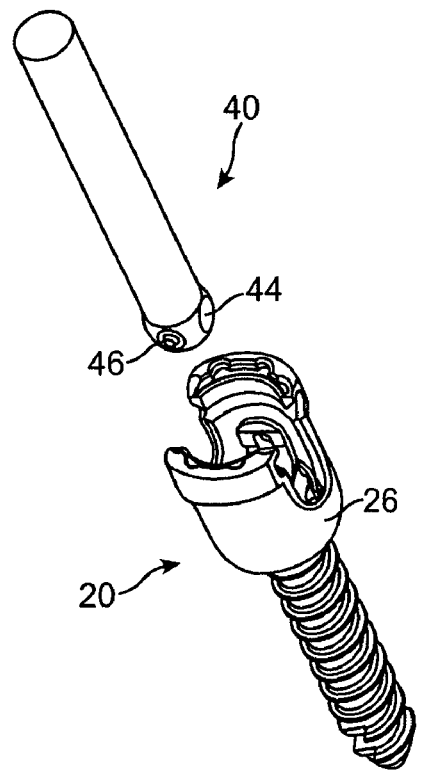
FIGS. 10A-10C illustrate a screw/seat/pivoting rod combination system in exploded, connected but not deployed, and post-rotation configurations, respectively.
Figure 10B:
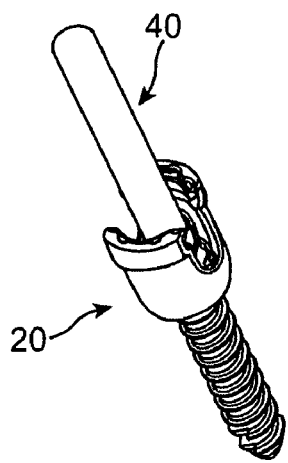
Figure 10C:
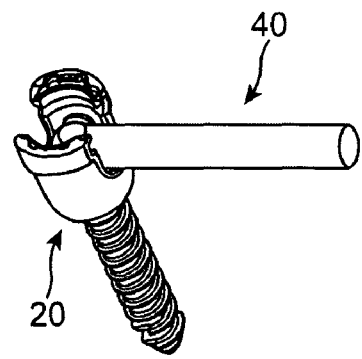

FIG. 10A-10C illustrates a method of rod installation which is typically accomplished just prior to the cap and set screw fixation shown in FIG. 9A-9D. Pivoting rod system 40 is disposed in the screw system 20. The chamfered nature of pins 46 eases the installation into the receiving holes of the coupler, as does the ramp 104 on the coupler. Once installed, as shown in FIG. 10B, the same may be rotated to approximately the position shown in FIG. 10C, though the actual amount of rotation will vary based on the shape of the patient's spine.

It should be noted that although FIGS. 10A and 10B illustrate the rod 40 in a vertical orientation that is substantially parallel to the screw orientation, the invention is not so limited. According to one variation of the invention, the rod 40 may be oriented 90 degrees in FIGS. 10A and 10B such that it is substantially perpendicular to the screw orientation and be capable of insertion into the seat. In another method of practicing the invention, the rod 40 can be oriented at any angle relative to the screw that permits insertion into the seat. The screw system 20 allows for the bone screw to be first set into the bone and then, following the insertion of the bone screw, the rod is attached in any of the various orientations of the rod relative to the screw just discussed. This two step process is advantageous in the event that patient anatomy makes it difficult to insert the rod-plus-screw combination at the same time. The system is versatile such that the rod may be attached first to the seat in the various orientations of the rod relative to the screw just described and then the entire system 20 (the rod-plus-screw combination) set into the bone simultaneously using instrumentation that grips the seat 26 at the flange 21 and/or recesses 23, for example, or the rod 40 itself. After the rod is attached, the cap is seated and locked. Prior to the locked configuration, that is a complete tightening of the set screw, and with or without the cap in position, the system retains two levels of freedom of motion. Firstly, the rod is free to be adjusted with respect to the seat and secondly, the seat is free to be adjusted relative to the screw. Hence, both the rod and the screw retain a degree of motion relative to seat, with or without the cap in place, which allows the clinician to custom orientate the seat with respect to the bone screw. The freedom of motion also permits the clinician to custom orientate the rod with respect to the seat with the system deployed inside the patient and in the unlocked configuration. This freedom of motion advantageously provides the surgeon with a much-needed, increased ease of implantation.

Figure 11A:
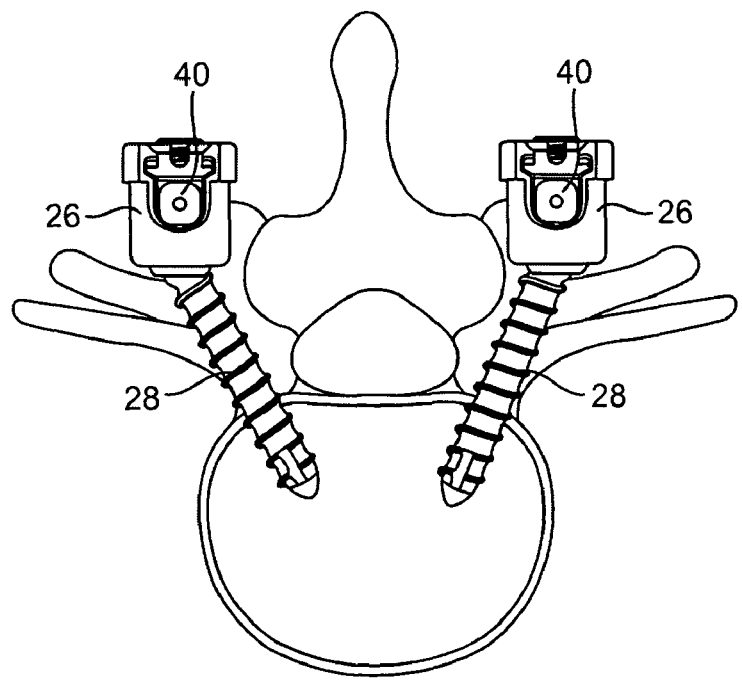
FIGS. 11A and 11B show the installed device in top and perspective views, respectively.
Figure 11B:
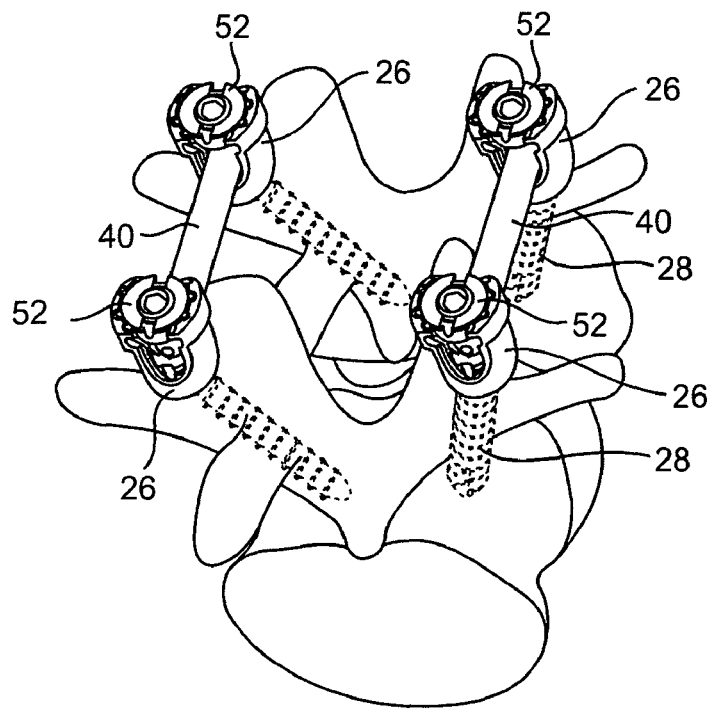

FIGS. 11A and 11B show a typical installation environment of the devices in two spinal segments of a patient.

Figure 12:
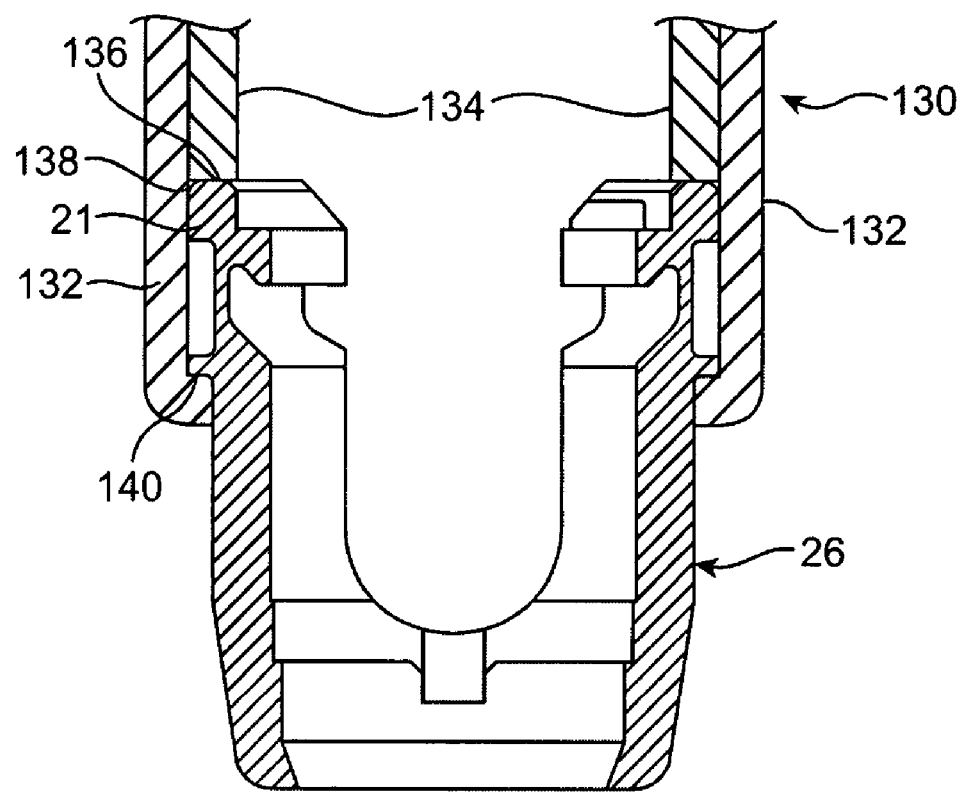
FIG. 12 illustrates a side cross-sectional view of the seat with a seat-gripping instrument engaging the seat according to one aspect of the invention.

FIG. 12 illustrates a side cross-sectional view of the seat 26 with a sectional view of a seat-gripping instrument 130 engaging the seat. The flange 21 of the seat 26 includes an upper surface 136, an outer surface 138 and a lower surface 140 and extends outwardly from the outer surface of the seat. Although FIG. 12 shows a single circumferentially continuous flange 21, the invention is not so limited and more than one flange may be formed.

Still referencing FIG. 12, the instrument 130 includes a first portion 132 and a second portion 134 interconnected with a handle portion (not shown). The first portion 132 of the instrument is configured to contact at least a portion of the flange outer surface 138 and/or at least a portion of the flange lower surface 140. The second portion 134 of the instrument is configured to slide with respect to the first portion 132 and contact the upper surface 136 of the flange as shown in FIG. 12. The second portion 134 is advanced to tighten against the upper surface and securely retain the seat within the instrument 130 for deployment into the patient.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

We claim:

1. A bone screw system, comprising:
 a bone screw including:
  a threaded section; and
  a screw head section integrally connected to the threaded section;
 a coupler including:
  a screw head receiving portion configured to receive at least a portion of the screw head section of the screw; and
  a rod receiving portion integral with the screw head receiving portion; the rod receiving portion configured to receive a rod;
 a seat having a first end and a second end; the seat including:
  at least one sidewall extending between the first end and the second end;
  a cap receiving portion configured to receive a cap at the first end;
  a coupler receiving portion configured to receive the coupler;
  a bottom opening at the second end;
  a top opening at the first end; and at least one rod channel defined by the sidewall; the at least one rod channel being interconnected with the top opening;

a cap configured to close the top opening of the seat; the cap having a top surface and a bottom surface interconnected by an outer surface and an inner surface; the inner surface defining a threaded set screw receiving portion; the outer surface defining at least one seat-engagement feature for engagement with the cap receiving portion of the seat;

a set screw having a top surface and a bottom surface interconnected by a threaded outer surface; the set screw configured to be threadingly engaged with the set screw receiving portion of the cap;

a retainer configured to retain the coupler inside the seat; and a rod having a first end and a second end; at least a portion of the rod configured to connect to the rod receiving portion of the coupler; and at least a portion of the screw head section disposed inside the screw head receiving portion of the coupler; the screw being inserted in the bottom opening of the seat and the coupler being retained inside the seat via the retainer pressed between the coupler and the seat; at least a portion of the rod being removably connected to the rod receiving portion of the coupler; the cap being removably inserted into the cap receiving portion of the seat and retained therein via the at least one seat-engagement feature on the outer surface of the cap; the set screw being disposed in the set screw receiving portion of the cap; the rod being disposed in the rod channel with the cap disposed in the cap receiving portion of the seat; upon advancement of the screw, the bottom surface of the set screw contacting at least a portion of the rod within the seat; and the bone screw and rod being locked into position with advancement of the set screw into the seat.

2. The system of claim 1, wherein the first end of the rod and coupler are configured to be connected together such that the rod is permitted to pivot at the first end.

3. The system of claim 2, wherein the rod and coupler include mating features adapted to connect together.

4. The system of claim 3, wherein the first end of the rod includes at least one pin and the rod receiving portion of the coupler includes at least one hole configured to receive the at least one pin.

5. The system of claim 4 wherein the at least one pin is spring loaded or extended or retracted by action of a screw.

6. The system of claim 1 wherein the rod receiving portion of the coupler includes at least one upstanding fork section.

7. The system of claim 6 wherein the at least one fork section is configured to allow flexion.

8. The system of claim 1 wherein the at least one seat engagement feature includes at least one wing and the cap receiving portion includes at least one corresponding wing groove for sliding engagement with the at least one wing.

9. The system of claim 8 wherein the at least one wing has a reverse angle surface such that motion of the cap relative to the seat upon set screw advancement substantially reduces splaying of the seat sidewall.

10. The system of claim 8 wherein the at least one wing groove includes a mechanical stop configured to abut the at least one wing to prevent rotation of the wing inside the wing groove.

11. The system of claim 1 wherein the at least one seat engagement feature includes at least one locking lug and the cap receiving portion includes at least one corresponding locking lug groove for sliding engagement with the at least one locking lug.

12. The system of claim 11 wherein the at least one locking lug groove includes a mechanical stop configured to abut the at least one locking lug to prevent rotation of the locking lug inside the locking lug groove.

13. The system of claim 1 wherein the at least one seat engagement feature includes at least one wing and at least one locking lug and the cap receiving portion includes at least one wing groove corresponding to the at least one wing and at least one locking lug groove corresponding to the at least one locking lug.

14. The system of claim 1 wherein the retainer comprises a retaining ring having at least one projection or key and the coupler has at least one corresponding keyway such that the retaining ring may only be disposed in a limited number of orientations on the coupler.

15. The system of claim 1 wherein the retaining ring is split.

16. The system of claim 1 wherein the coupler includes a lip and the retaining ring being disposed on the lip.

17. The system of claim 1 wherein the coupler includes at least one slit to allow the screw head receiving portion of the coupler to flex.

18. The system of claim 1 wherein the coupler includes a tapered surface and the seat includes a corresponding tapered surface.

19. The system of claim 1 wherein the set screw includes at least one feature selected from the group consisting of a dome, a raised surface, a nipple, an aperture and a dome with an aperture.

20. The system of claim 1 wherein the bone screw includes a socket for receiving a driving element.

21. The system of claim 1 wherein the cap includes a groove and recess to receive an insertion tool.

22. The system of claim 1 wherein the seat and coupler are configured to allow approximately 60 degrees of polyaxial rotation of the bone screw relative to the seat.

23. The system of claim 1 wherein the set screw includes a flange extending outwardly from a circumference of the set screw to serve as a stop to prevent the set screw from being backed-out as the set screw is retracted upwardly with respect to the cap.

24. A bone screw system having a locked configuration and an unlocked configuration, comprising:

a rod;

a seat having a first end portion and a second end portion; the first end portion of the seat comprising two upstanding forks defining a substantially U-shaped slot configured to receive a portion of the rod; a distal end portion of the two upstanding forks comprising a cap receiving portion configured to receive a cap during use; the second end portion comprising an opening configured to be disposed about a head of a bone screw during use;

a coupler having a first end portion and a second end portion; the first end portion of the coupler comprising two upstanding forks defining a substantially U-shaped slot configured to receive first end portion of the rod such that a second end portion of the rod is pivotable about the first end portion of the rod disposed in the coupler during use; the second end portion of the coupler comprising a recess configured to receive a head of a bone screw during use; wherein the U-shaped slot of the coupler and the U-shaped slot of the seat substantially align with one another during use such that the rod is pivotable about the first end portion of the rod between a vertical position and a horizontal position during use, wherein the vertical position comprises the rod extending longitudinally through upper openings in the U-shaped slots, and wherein the horizontal position comprises the rod extending laterally through side openings in the U-shaped slots;

a bone screw having a first end and a second end; at least a portion of the first end of the bone screw comprising the head being disposed inside the recess of the coupler and within the opening of the seat; the screw having a range of motion relative to the seat when in the unlocked configuration;

a lock down mechanism removably disposed inside the cap receiving portion of the distal end of the seat; at least a portion of the rod being located between the lock down mechanism and the first end of the bone screw; the lock down mechanism being operable between a locked configuration and the unlocked configuration such that the rod or the bone screw is locked into position as the lock down mechanism operates from the unlocked configuration to the locked configuration.

25. The system of claim 24 wherein the coupler is retained inside the seat such that the bone screw and rod are coupled to the seat via the coupler.

26. The system of claim 24 wherein the rod is removably coupled to the coupler.

27. The system of claim 24 further including a retaining ring disposed between the coupler and the seat to retain the coupler inside the seat.

28. The system of claim 27 wherein the retaining ring comprises at least one projection or key and the coupler has at least one corresponding keyway such that the retaining ring may only be disposed in a limited number of orientations on the coupler.

29. The system of claim 24 wherein the lock down mechanism includes a cap and a set screw.

30. The system of claim 29 wherein the cap includes at least one seat engagement feature on an outer surface of the cap and the set screw is disposed inside a threaded bore passing through the cap.

31. The system of claim 30 wherein the at least one seat engagement feature includes at least one wing and at least one locking lug.

32. The system of claim 29 wherein the coupler is retained inside the seat such that the bone screw and rod are coupled to the seat via the coupler and wherein operation from the unlocked configuration to the locked configuration includes advancing the set screw towards the interior of the seat to contact the rod and tighten the coupler around at least a portion of the first end of the bone screw retained within the coupler; the rod being locked into position between the coupler and the set screw.

33. The system of claim 29 wherein the set screw includes a flange extending outwardly from the circumference of the set screw to serve as a stop to prevent the set screw from being backed-out as the set screw is retracted upwardly with respect to the cap.

34. The system of claim 24 wherein the lock down mechanism is operable between a locked configuration and an unlocked configuration such that the rod or the bone screw is locked into position as the lock down mechanism operates from the unlocked configuration to the locked configuration; and the other of the rod or the bone screw is also locked into position as the lock down mechanism operates from the unlocked configuration to the locked configuration.

35. The system of claim 34 wherein the other of the rod or the bone screw is locked into position simultaneously with one of the rod or the bone screw as the lock down mechanism operates from the unlocked configuration to the locked configuration.

36. The system of claim 34 wherein the other of the rod or the bone screw is locked into position prior to one of the rod or the bone screw as the lock down mechanism operates from the unlocked configuration to the locked configuration.

37. The system of claim 24 wherein the rod comprises at least one pin configured to be disposed in a complementary recess of the two or more upstanding forks of the coupler, and wherein the at least one pin is spring loaded or extended or retracted by action of a screw.

38. A bone screw system, comprising:
a rod;
a bone screw having a head;
a substantially U-shaped seat comprising an opening extending longitudinally there through, wherein the opening comprises:
a bottom opening portion disposed at least partially about the head of the bone screw during use; and
an upper opening portion defining a slot for receiving first end portion of the rod during use, wherein the slot comprises an upper opening portion and a side opening portion;
a substantially U-shaped coupler comprising:
a bone screw receiving portion comprising a recess configured to couple to a head of the bone screw during use; and
a rod receiving portion comprising a cradle configured to pivotably couple to the first end portion of the rod during use, wherein the cradle comprises an upper opening portion and a side opening portion;
wherein the coupler is disposed concentrically inside the opening of the seat during use such that the upper and side opening portions of the seat and the coupler are substantially aligned with one another, and wherein the first end portion of the rod is pivotably coupled to the cradle of the coupler during use such that the rod is pivotable about the first end portion of the rod between a vertical position and a horizontal position, wherein the vertical position comprises the rod extending in a substantially longitudinally direction through the upper opening portions, and wherein the horizontal position comprises the rod extending in a substantially lateral direction through the side opening portions during use, wherein when the rod is in the horizontal position two upstanding forks defining at least a portion of the substantially U-shaped coupler rise at least above a midline of the rod during use.

39. The system of claim 38 further including a retaining ring configured to retain the coupler inside the seat; the retaining ring being disposed between the seat and the coupler in a press-fit engagement.

40. The system of claim 39 wherein the retaining ring comprises at least one projection or key and the coupler has at least one corresponding keyway such that the retaining ring may only be disposed in a limited number of orientations on the coupler.

41. The system of claim 38 wherein the rod receiving portion includes two upstanding forks.

42. The system of claim 38 wherein the rod is removably coupled to the rod receiving portion of the coupler.

43. The system of claim 38 wherein the rod includes a first end and a second end; the rod and coupler being configured such that the first end of the rod is coupled to the coupler and the rod pivots about the first end of the rod.

44. The system of claim 43 wherein the rod includes at least one outwardly extending pin proximate the first end of the rod configured to couple to the rod receiving portion of the coupler.

45. The system of claim 44 wherein the at least one outwardly extending pin is spring loaded or extended or retracted by action of a screw.

46. The system of claim 38 wherein the coupler includes at least one slit in the bone screw receiving portion such that at least a portion of the bone screw receiving portion can flex.

47. The system of claim 38 further including a closure mechanism that includes seat engagement features on the outer surface for engaging with the seat; wherein the seat includes a closure mechanism receiving portion at an upper end the upper opening portion of the seat; the closure mechanism being disposed in in-the closure mechanism receiving portion of the seat.

48. The system of claim 38 wherein the upper opening of the seat further includes at least one rod channel extending there through.

49. The system of claim 38 wherein the recess of the bone screw receiving portion includes an opening shaped complementary to the head of the bone screw.

50. The system of claim 38 wherein the coupler includes a bore extending between the rod receiving portion and the bone screw receiving portion.

51. A bone screw system, comprising:
a bone screw;
a seat having a first end and a second end; the seat retaining the bone screw inside the seat; the seat including:
  at least one sidewall extending between the first end and the second end; and
  a top opening at the first end, the opening defining a slot for receiving an end portion of the rod during use, wherein the slot comprises an upper opening portion and a side opening portion; and
  a cap receiving portion in the at least one sidewall; the cap receiving portion configured to receive a cap within the seat at the first end; the cap receiving portion having at least one wing groove; the at least one wing groove having an upper surface;
a cap being configured to close the top opening of the seat; the cap having a top surface and a bottom surface interconnected by an outer surface and an inner surface; the inner surface defining a set screw receiving portion; the outer surface of the cap defining at least one wing lug extending outwardly from the outer surface of the cap; the wing lug being configured to mate with the at least one wing groove of the seat by rotation of the wing lug into the wing groove;
a set screw having a top surface and a bottom surface interconnected by a threaded outer surface; the set screw being configured to be threadingly engaged with the set screw receiving portion of the cap; the set screw being inserted into the set screw receiving portion of the cap;
the cap being removably inserted into the cap receiving portion of the seat closing the top opening; with the cap in the seat, the cap being rotated to position the at least one wing lug inside the at least one wing groove;
the set screw being advanced into the seat; set screw advancement being biased by the seat raising the cap such that the at least one wing lug contacts the upper surface of the wing groove, secures the cap to the seat and prevents splaying of the seat sidewall;
a rod; and
a coupler configured to be disposed within the seat, the coupler comprising:
  a lower portion comprising a bone screw receiving portion configured to couple to a head of the bone screw during use; and
  an upper portion comprising a rod receiving cradle configured to rotatably couple to the end portion of the rod during use, wherein the cradle comprises an upper opening portion and a side opening portion;
wherein the coupler is disposed concentrically inside the opening of the seat during use such that the upper and side opening portions of the seat and the coupler are substantially aligned with one another, and wherein the end portion of the rod is rotatably coupled to the cradle of the coupler during use such that the rod is rotatable between a vertical position and a horizontal position, wherein the vertical position comprises the rod extending in a substantially longitudinally direction through the upper opening portions, and wherein the horizontal position comprises the rod extending in a substantially lateral direction through the side opening portions during use.

52. The system of claim 51 wherein the cap receiving portion further includes at least one locking lug groove; the cap further including at least one locking lug extending outwardly from the outer surface of the cap; the locking lug being configured to mate with the at least one locking lug groove of the seat by rotation of the locking lug into the locking lug groove.

53. The system of claim 52 wherein the at least one locking lug is configured to be inserted into the side opening portion of the slot of the seat and rotated into the locking lug groove form its location in the rod channel.

54. The system of claim 51 wherein the locking lug groove includes a mechanical stop configured to stop rotation of the locking lug inside the locking lug groove.

55. The system of claim 51 wherein the locking lug groove includes a recess configured to receive the locking lug when the cap is raised relative to the seat upon set screw advancement; the recess preventing couter-rotation of the locking lug while disposed inside the recess.

56. The system of claim 51 wherein the set screw includes a flange extending outwardly from the circumference of the set screw to serve as a stop to prevent the set screw from being backed-out as the set screw is retracted upwardly with respect to the cap.

57. The system of claim 51 wherein the seat includes at least one rod channel formed in the sidewall.

58. The system of claim 57 wherein the wing lug is configured to be inserted into the at least one rod channel and rotated into the wing lug groove form its location in the rod channel.

59. The system of claim 51 wherein the rod comprises at least one pin configured to be disposed in a complementary recess of the cradle of the coupler, and wherein the at least one pin is spring loaded or extended or retracted by action of a screw.

60. A bone screw system, comprising:
a bone screw including:
  a threaded section; and
  a screw head section integrally connected to the threaded section;
a coupler including:
  a screw head receiving portion configured to receive at least a portion of the screw head section of the screw; and
  a rod receiving portion integral with the screw head receiving portion; the rod receiving portion configured to receive a rod;

a seat having a first end and a second end; the seat including:
  at least one sidewall extending between the first end and the second end;
  a cap receiving portion configured to receive a cap at the first end;
  a coupler receiving portion configured to receive the coupler;
  a bottom opening at the second end;
  a top opening at the first end; and
  at least one rod channel defined by the sidewall; the at least one rod channel being interconnected with the top opening;
a cap configured to close the top opening of the seat; the cap having a top surface and a bottom surface interconnected by an outer surface and an inner surface; the inner surface defining a threaded set screw receiving portion; the outer surface defining at least one seat-engagement feature for engagement with the cap receiving portion of the seat;
a set screw having a top surface and a bottom surface interconnected by a threaded outer surface; the set screw configured to be threadingly engaged with the set screw receiving portion of the cap;
a retainer configured to retain the coupler inside the seat; wherein the retainer comprises a retaining ring having at least one projection or key and the coupler has at least one corresponding keyway such that the retaining ring may only be disposed in a limited number of orientations on the coupler and
a rod having a first end and a second end; at least a portion of the rod configured to connect to the rod receiving portion of the coupler; the first end of the rod and coupler are configured to be connected together such that the rod is permitted to pivot at the first end; the rod and coupler include mating features adapted to connect together; the first end of the rod includes at least one pin and the rod receiving portion of the coupler includes at least one hole configured to receive the at least one pin; and the at least one pin is spring loaded or extended or retracted by action of a screw; and
at least a portion of the screw head section disposed inside the screw head receiving portion of the coupler; the screw being inserted in the bottom opening of the seat and the coupler being retained inside the seat via the retainer pressed between the coupler and the seat; at least a portion of the rod being removably connected to the rod receiving portion of the coupler; the cap being removably inserted into the cap receiving portion of the seat and retained therein via the at least one seat-engagement feature on the outer surface of the cap; the set screw being disposed in the set screw receiving portion of the cap; the rod being disposed in the rod channel with the cap disposed in the cap receiving portion of the seat; upon advancement of the screw, the bottom surface of the set screw contacting at least a portion of the rod within the seat; and the bone screw and rod being locked into position with advancement of the set screw into the seat.

61. A bone screw system, comprising:
a bone screw including:
  a threaded section; and
  a screw head section integrally connected to the threaded section;
a coupler including:
  a screw head receiving portion configured to receive at least a portion of the screw head section of the screw; and
  a rod receiving portion integral with the screw head receiving portion; the rod receiving portion configured to receive a rod;
a seat having a first end and a second end; the seat including:
  at least one sidewall extending between the first end and the second end;
  a cap receiving portion configured to receive a cap at the first end;
  a coupler receiving portion configured to receive the coupler;
  a bottom opening at the second end;
  a top opening at the first end; and
  at least one rod channel defined by the sidewall; the at least one rod channel being interconnected with the top opening;
a cap configured to close the top opening of the seat; the cap having a top surface and a bottom surface interconnected by an outer surface and an inner surface; the inner surface defining a threaded set screw receiving portion; the outer surface defining at least one seat-engagement feature for engagement with the cap receiving portion of the seat;
a set screw having a top surface and a bottom surface interconnected by a threaded outer surface; the set screw configured to be threadingly engaged with the set screw receiving portion of the cap;
a retainer configured to retain the coupler inside the seat; and
a rod having a first end and a second end; at least a portion of the rod configured to connect to the rod receiving portion of the coupler; and
at least a portion of the screw head section disposed inside the screw head receiving portion of the coupler; the screw being inserted in the bottom opening of the seat and the coupler being retained inside the seat via the retainer pressed between the coupler and the seat; at least a portion of the rod being removably connected to the rod receiving portion of the coupler; the cap being removably inserted into the cap receiving portion of the seat and retained therein via the at least one seat-engagement feature on the outer surface of the cap; the set screw being disposed in the set screw receiving portion of the cap; the rod being disposed in the rod channel with the cap disposed in the cap receiving portion of the seat; upon advancement of the screw, the bottom surface of the set screw contacting at least a portion of the rod within the seat; and the bone screw and rod being locked into position with advancement of the set screw into the seat.

62. A bone screw system, comprising:
a bone screw;
a seat having a first end and a second end; the seat retaining the bone screw inside the seat; the seat including:
  at least one sidewall extending between the first end and the second end; and
  a top opening at the first end; and
  a cap receiving portion in the at least one sidewall; the cap receiving portion configured to receive a cap within the seat at the first end; the cap receiving portion having at least one wing groove; the at least one wing groove having an upper surface;
a cap being configured to close the top opening of the seat; the cap having a top surface and a bottom surface interconnected by an outer surface and an inner surface; the inner surface defining a set screw receiving portion; the outer surface of the cap defining at least one wing lug extending outwardly from the outer surface of the cap; the wing lug being configured to mate with the at least one wing groove of the seat by rotation of the wing lug into the wing groove;

a set screw having a top surface and a bottom surface interconnected by a threaded outer surface; the set screw being configured to be threadingly engaged with the set screw receiving portion of the cap; the set screw being inserted into the set screw receiving portion of the cap; the set screw having a flange extending outwardly from the circumference of the set screw to serve as a stop to prevent the set screw from being backed-out as the set screw is retracted upwardly with respect to the cap the cap being removably inserted into the cap receiving portion of the seat closing the top opening; with the cap in the seat, the cap being rotated to position the at least one wing lug inside the at least one wing groove;

the set screw being advanced into the seat; set screw advancement being biased by the seat raising the cap such that the at least one wing lug contacts the upper surface of the wing groove, secures the cap to the seat and prevents splaying of the seat sidewall.

63. A bone screw system, comprising:
a bone screw comprising:
  a threaded section; and
  a screw head section;
a coupler comprising:
  a lower coupler portion having a screw head receiving portion comprising a recess configured to receive the screw head section of the bone screw, wherein the recess is shaped complementary to the screw head section, and wherein an exterior wall defining the recess comprises a plurality of slits to facilitate compression of the walls about the portion of the screw head disposed in the recess;
  an upper coupler portion having a rod receiving portion comprising two upstanding forks defining a substantially U-shaped slot configured to receive a portion of a rod, wherein the two upstanding forks comprise a rod pin opening configured to receive a rod pin of the rod; and
  a longitudinal opening extending between the slot of the upper coupler portion and the recess of the lower coupler portion, wherein the longitudinal opening configured to provide access to the screw head section of the bone screw when the screw head is disposed in the recess;
a seat having a longitudinal opening in which the coupler is configured to be disposed, the longitudinal opening comprising:
  a lower seat portion configured to be disposed about a portion of the screw head section of the bone screw during use, wherein the lower seat portion comprising a coupler receiving portion configured to engage the coupler during use; and
  an upper seat portion having a rod receiving portion comprising two upstanding forks defining a substantially U-shaped slot configured to receive a portion of the rod, wherein an upper end of the two upstanding forks comprises a cap receiving portion configured to receive a cap during use;
a cap configured to be disposed in the cap receiving portion of the seat during use to at least partially enclose the upper seat end during use, the cap comprising:
  an outer surface defining at least one seat-engagement feature for engagement with a complementary portion of the cap receiving portion of the seat; and
  a set screw receiving portion comprising a longitudinal threaded opening extending between upper and lower surfaces of the cap;
a retainer configured to retain the coupler inside the seat, wherein the retainer is configured to couple to an interior of the seat, wherein the retainer is disposed above a portion of the coupler, and wherein the retainer is configured to engage the portion of the coupler to inhibit movement of the coupler through the upper end of the seat;
a rod having a coupler engagement portion comprising one or more pins configured to engage the rod pin opening of the two upstanding forks of the coupler during use; and
a set screw configured to be disposed in the set screw receiving portion of the cap during use, the set screw comprising an outer surface comprising an external thread configured to be threading engaged with the threaded opening of the set screw receiving portion of the cap during use, wherein advancement of the set screw is configured to substantially inhibit movement of the rod relative to the bone screw.

64. The system of claim 63, wherein advancement of the set screw is configured to cause a lower portion of the set screw to engage a portion of the rod to generate a locking force configured to substantially inhibit movement of the rod relative to the bone screw.

65. The system of claim 63, wherein the set screw directly contacts the rod.

66. The system of claim 63, wherein:
an exterior surface of the wall defining the recess of the lower coupler comprises an external tapered ramp;
the coupler receiving portion of the seat comprises an interior surface of the longitudinal opening, wherein the an internal tapered ramp complementary to the external tapered ramp of the coupler, and
engagement of the internal ramp with the external ramp is configured to cause compression of the walls about the portion of the screw head disposed in the recess to inhibit movement of the coupler relative to the bone screw during use.

67. The system of claim 63, wherein the one or more pins are integral with the body of the rod.

68. The system of claim 63, wherein the U-shaped slot of the coupler and the U-shaped slot of the seat substantially align with one another during use such that the rod is rotatable between a vertical position and a horizontal position, wherein the vertical position comprises the rod extending longitudinally through upper openings in the U-shaped slots, and wherein the horizontal position comprises the rod extending laterally through side openings in the U-shaped slots.

* * * * *